US006767738B1

(12) United States Patent
Gage et al.

(10) Patent No.: US 6,767,738 B1
(45) Date of Patent: Jul. 27, 2004

(54) METHOD OF ISOLATING ADULT MAMMALIAN CNS-DERIVED PROGENITOR STEM CELLS USING DENSITY GRADIENT CENTRIFUGATION

(75) Inventors: Fred H. Gage, La Jolla, CA (US); Theo Palmer, San Carlos, CA (US); Francis G. Safar, Irvine, CA (US); Jun Takahashi, Kyoto (JP); Masayo Takahashi, Kyoto (JP)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/913,192
(22) PCT Filed: Feb. 11, 2000
(86) PCT No.: PCT/US00/03596
§ 371 (c)(1),
(2), (4) Date: Feb. 12, 2002
(87) PCT Pub. No.: WO00/47718
PCT Pub. Date: Aug. 17, 2000

Related U.S. Application Data

(60) Provisional application No. 60/155,871, filed on Sep. 24, 1999, and provisional application No. 60/119,642, filed on Feb. 11, 1999.

(51) Int. Cl.[7] .............................. C12N 5/02; C12N 5/08
(52) U.S. Cl. ...................... 435/325; 435/366; 435/368; 435/378
(58) Field of Search ................................ 435/325, 352, 435/354, 363, 366, 368, 378, 7.21, 29, 240.1, 240.2, 240.21, 240.23, 384, 405, 406, 395, 402; 536/23.1

(56) References Cited
U.S. PATENT DOCUMENTS
6,033,906 A * 3/2000 Anderson .................. 435/325

OTHER PUBLICATIONS

Strong and Garruto (Oct. 1989) Isolation of Fetal Mouse Motor Neurons on Discontinuous Percoll Density Gradient. In Vitro Cellular and Developmental Biology 25(10): 939–945.*

Marmur et al. (1998) Isolation and Developmental Characterization of Cerebral Cortical Multipotent Progenitors. Developmental Biology 204: 577–591.*

Gage et al. (1995) Isolation, Characterization, and Use of Stem Cells from the CNS. Annu. Rev. Neurosci. 18: 159–192.*

* cited by examiner

*Primary Examiner*—Gary Kunz
*Assistant Examiner*—Christopher James Nichols
(74) *Attorney, Agent, or Firm*—Foley & Lardner; Stephen E. Reiter

(57) ABSTRACT

The present invention is directed to methods of repairing damaged or diseased, specialized or differentiated tissue in mature animals, particularly neuronal tissue such as retinas. In particular, the invention relates to transplantation of adult, hippocampus-derived progenitor cells into a selected neural tissue site of a recipient. These cells can functionally integrate into mature and immature neural tissue. The invention encompasses, in one aspect, repopulating a retina of a dystrophic animal with neurons, by injecting clonally derived, adult central nervous system derived stem cells (ACSC) derived from a healthy donor animal into an eye of the dystrophic recipient. Herein disclosed is the first successful and stable integration of clonally derived ACSC into same-species but different strain recipients (e. g., Fischer rat-derived adult hippocampal derived progenitor cells (AHPCs) into dystrophic RCS rats). Surprisingly, AHPCs were also found to integrate successfully into a xenogeneic recipient (e.g., rat AHPCs into the retina of dystropic rd-I mice).

13 Claims, No Drawings

METHOD OF ISOLATING ADULT MAMMALIAN CNS-DERIVED PROGENITOR STEM CELLS USING DENSITY GRADIENT CENTRIFUGATION

RELATED APPLICATIONS

This application is a national phase entry of PCT/US00/03596 (filed Feb. 11, 2000 under 35 U.S.C. §371; which in turn claims the benefit of U.S. Provisional Application No. 60/119,642, filed Feb. 11, 2000, now abandoned, and U.S. Provisional Application No. 60/155,871, filed 09/24/1999, now abandoned.

FIELD OF THE INVENTION

The present invention relates to the fields of stem cells and gene therapy.

BACKGROUND OF THE INVENTION

Cell proliferation in the adult mammalian brain is ubiquitous but is largely confined to the measured production of glia. Except for discrete regions in the hippocampus and the subventricular zone (SVZ), neurogenesis is conspicuously absent. The reasons why these areas continue to generate neurons are unknown, but primary cell cultures from the adult rodent brain are beginning to provide some insights. Cultures initiated from adult SVZ or hippocampal tissues contain proliferative neuronal and glial-restricted progenitors as well as multipotent precursors with the characteristics of neural stem cells, i.e., the ability to self-renew and the ability to generate both neurons and glia.

It has been suggested that stem cells may be more widely distributed since cells from non-neurogenic areas repeatedly passaged in the presence of high concentrations of basic fibroblast growth factor (FGF-2) appear to begin to generate neurons in vitro. This observation is consistent with the isolation of neuronal progenitors from these areas, but the protracted times in culture suggests another explanation. It is known that stem cell cultures initiated from hippocampal tissues will spontaneously transform, due to accumulated genetic abnormalities. Abnormalities in chromosome number can occur in as little as 30 population doublings and, as cells become increasingly aneuploid, it is possible that glial-restricted progenitors acquire capabilities beyond those available in vivo.

With existing methodologies, it has been difficult to distinguish between the activation of a latent potential vs. in vitro mutation. Unlike fibroblast tissues, which are easily dissociated and yield relatively abundant precursor populations, adult tissues yield few progenitors and the progenitor preparations are contaminated with differentiated cells and tissue debris. The myelin-rich debris inhibits cell attachment and growth while differentiated cells complicate the evaluation of lineage potential in acutely isolated cultures. Past studies have evaluated "progenitors" only after repeated passaging had eliminated the debris and differentiated cells. Even if these cells had remained diploid, they may have been dramatically altered in prolonged culture. Accordingly, there exists a need in the art for isolating a "clean" (i.e., more enriched) cell population containing putative progenitor and stem cells, so that they can be studied without contaminating debris.

The ability to isolate progenitor or stem cells from a variety of tissues would provide a basis for therapeutic applications using these immature cell types. Neural tissue, in particular, comprises a unique biological system that presents unique therapeutic challenges. Damaged neural tissue has proven very difficult to repair or replace. To facilitate the repair or replacement of neural tissue, scientists have focused their efforts on the identification, isolation and use of neuronal stem cells (or "progenitor cells"). With an appropriately pluripotent neural progenitor or stem cell, regeneration or augmentation of a variety of neural cell types is a possibility. Indeed, with a progenitor cell exhibiting an even more widely ranging plasticity, the regeneration or augmentation of a variety of cell types should be possible. Similarly, the stem cell would be a useful vehicle for introducing exogenous genetic material, as desired to achieve therapeutic results.

Occular tissue, in particular the retina, represents a highly specialized neural structure for which repair is often required. For example, the eye is frequently subjected to environmentally or genetically induced injury. As a result, appropriately plastic stem cells would present a valuable vehicle for repair, replacement and/or genetic manipulation (e.g., gene therapy). Although physical damage to the eye may require merely replacing damaged cells with a cell type exhibiting the required plasticity, genetically mediated degeneration of occular tissue presents a more complex challenge.

In many instances, the exact molecular mechanisms that mediate occular or retinal degeneration are poorly understood. Grafting genetically modified cells provides an effective method for evaluating the relative impact of candidate molecules on retinal biology. In addition, the ability to introduce engineered cells may provide a considerable therapeutic benefit for a variety of progressive degenerative diseases. Past attempts to use cell grafts for the delivery of transgene products in the eye have met with mixed success. Heterotypic grafts of non-neural cells fail to integrate and often physically disrupt the normal retinal architecture; Planck, S. R., et al. *Curr. Eye Res.* 11: 1031 (1992). Homotypic fibroblast tissue grafts show some integration but are not amenable to genetic manipulation prior to implantation. See, for example, Seiler, M. J. & Aramant, R. B., Transplantation of embryonic retinal donor cells labelled with BrdU or carrying a genetic marker to adult retina, Exp. Brain Res. 105: 59–66 (1995); Gouras, P., Du, J., Kjeldbye, H., Yamamoto, S., Zack, D. J., Long-term photoreceptor transplants in dystrophic and normal mouse retina, 35:3145–3153 (1994); and Gouras, P., Du, J., Kjeldbye, H., Kwun R., Lopez, R., Zack, D. J., Transplanted photoreceptors identified in dystrophic mouse retina by a transgenic reporter gene, *Invest Ophthalmol. Vis. Sci.* 32: 3167–3174 (1991). Grafts of retinal cell lines (i.e., immortalized cell lines) partially overcome these problems. Trisler, D., Rutin, J. & Pessac, B., Retinal engineering: engrafted neural cell lines locate in appropriate layers, *Proc. Natl. Acad. Sci. U.S.A.* 93: 6269–274 (1996); del Cerro, M., Notter, M. F., Seigel, G., Lazar, E., Chader, G., del Cerro, C., Intraretinal xenografts of differentiated human retinoblastoma cells integrate with the host retina, *Brain Res.*, 583:12–22 (1992). However, immortalized cells present potential risks of tumor formation that makes their use less than ideal.

Several groups have reported heterotypic transplants of neuronal progenitor cells, immortalized neural cell lines or embryonic neural precursors into the CNS. To date, however, none of these studies has shown satisfactory diversity and distribution of cell types to render such cells broadly useful either as cell source for cell replacement therapy or-for the expression of transgenes in the host tissue.

In recent years, significant attention has been directed toward identification and characterization of very immature progenitor cells in the adult brain. Gage, F. H., Ray, J. & Fisher, L. J., Isolation, characterization, and use of stem cells from the CNS, *Annu. Rev. Neurosci.*, 18:159–192 (1995). Additionally, it has been reported that stem cell-like multipotent progenitors can be isolated from adult hippocampus of rats, expanded in vitro and subsequently grafted into adult hippocampus and olfactory bulb where they demonstrate site-specific neuronal differentiation. See, for example, Palmer, T. D., Talkahashi, J., Gage, F. H., The rat hippocampus contains primordial neural stem cells, *Mol. Cell. Neurosci.*, 8: 389 (1997); Palmer, T. D., Ray, J. & Gage, F. H. FGF-2-responsive neuronal progenitors reside in proliferative and quiescent regions of the adult rodent brain, *Mol. Cell Neurosci.* 6: 474–486 (1995); Gage, F. H., Coates, P. W., Palmer, T. D., et al. Survival and differentiation of adult neuronal progenitor cells transplanted to the adult brain. *Proc. Natl. Acad. Sci. U. S. A.* 92:11879–11883 (1995); and Suhonen, J. O., Peterson, D. A., Ray,J. & Gage, F. H. Differentiation of adult hippocampus-derived progenitors into olfactory neurons in vivo, Nature 383:624–627 (1996). Some of the phenotypes generated in the olfactory bulb are not found in the hippocampus, suggesting that the most immature of these stem-like cells may retain considerable plasticity.

As part of the central nervous system, both developmentally and phenotypically, the retina shares the recalcitrance of brain and spinal cord with respect to functional repair. This is unfortunate in that, among heritable conditions alone, there are over 100 examples of diseases involving the loss of retinal neurons. Bird, A. C., Retinal photoreceptor dystrophies L. I. Edward Jackson Memorial Lecture, see comments. Am J Ophthalmol 119, 543–62, (1995); Simunovic, M. P., and Moore, A. T., The cone dystrophies. Eye 12,.553–65 (1998). One strategy for replacing these cells has been to transplant retinal tissue from healthy donors to the retina of the diseased host (see, for example, Gouras, P., Du, J. , Kjeldbye, H., Yamamoto, S., and Zack, D. J., Long-term photoreceptor transplants in dystrophic and normal mouse retina. Invest Ophthalmol Vis Sci 35, 3145–53 (1994); Silverman, M. S., and Hughes, S. E., Transplantation of photoreceptors to light-damaged retina. Invest Ophthalmot Vis Sci 30, 1684–90 (1989)). While the results of such studies have been encouraging in terms of graft survival, the problem of integration between graft and host has proved to be daunting. The graft-host interface is often well demarcated histologically, with ultrastructural studies revealing the presence of a dense glial scar across which few neurites are seen to cross. Ivert, L., Gouras, P., Naeser, P., and Narfstrom, K., Photoreceptor allografts in a feline model of retinal degeneration. Graefes Arch Clin Exp Ophffidmol 236, 844–52 (1998).

Thus, there exists a need to develop methods for the isolation and exploitation of stem cells which can, in turn, be used as a therapeutic agent and/or as a vehicle for additional manipulation of gene-based therapeutics in order to treat damaged or diseased tissue, particularly neuronal tissue, and more particularly ocular tissue.

BRIEF DESCRIPTION OF THE INVENTION

The present invention is directed to methods of enriching a cell population for stem cells and/or stein cell precursors. Stem cells isolated by the present invention are pluripotent, however, precursor stem cells are not. In another embodiment of the present invention there is provided a method for treating precursor stem cells in a manner that produces stem cells. Stem cells, whether isolated by invention methods or generated by invention methods are useful in repairing damaged or diseased, specialized or differentiated tissue in mature animals, particularly neuronal tissue such as retinas.

One embodiment of the present invention relates to transplantation of adult, hippocampus (HC)-derived progenitor cells into a selected neural tissue site of a recipient. These cells can functionally integrate into mature and immature neural tissue. The invention encompasses, in one aspect, repopulating a retina of a dystrophic animal with neurons, by injecting clonally derived, adult central nervous system derived stem cells (ACSC) derived from a healthy donor animal into an eye of the dystrophic recipient. Herein disclosed is the first successful and stable integration of clonally derived ACSC/ACPC into same-species but different strain recipients (e.g., Fischer rat-derived adult hippocampal derived progenitor cells (AHPCs) into dystrophic RCS rats). Surprisingly, AHPCs were also found to integrate successfully into a xenogeneic recipient (e.g., rat AHPCs into the retina of dystrophic rd-I mice).

DETAILED DESCRIPTION OF THE INVENTION

In accordance with the present invention there is provided a method for obtaining Adult Mammalian Stem Cells or Adult Mammalian Progenitor stem Cells from tissue (AMSC and AMPC, respectively), said method comprising subjecting dissociated mammalian tissue to one or more buoyancy-based separation systems. In one aspect of this embodiment, there is provided a method for obtaining adult mammalian CNS-derived progenitor cells (ACPC) or Adult Mammalian CNS-derived Stem Cells (ACSC) from a cell population containing adult mammalian central nervous system (CNS) tissue, said method comprising subjecting dissociated mammalian CNS tissue to one or more buoyancy-based separation systems.

In another embodiment of the present invention there are provided adult mammalian stem cells or adult mammalian progenitor cells isolated by invention methods. In a specific aspect of this embodiment, there are provided adult CNS-derived progenitor cells (ACPC) or adult mammalian CNS-derived stem cells (ACSC) isolated by subjecting dissociated mammalian CNS tissue to one or more buoyancy-based separation systems.

In another embodiment of the present invention AMSC and AMPC have the ability to adapt to a heterotypic environment.

As used herein, "stem cells" means cells that are self-renewing and multipotent (i.e., that are not lineage restricted). Stem cells includes AMSC and ACSC as defined herein. Stem cells are characterized as both self-renewing and able to differentiate. "Progenitor" or "precursor" cells means an undifferentiated cell whose lineal descendants differentiate along the appropriate pathway to produce a fully differentiated phenotype (i.e., cells with a restricted lineage). For example, neural stem cells isolated from the hippocampus (HC) or the subventricular zone, are self renewing and able to generate, in vitro, multiple types of cells including neurons, glia and even hematopoetic cells. In contrast, neural progenitor or precursor cells are lineage restricted and while self-renewing, only generate glia in vitro. Progenitor or precursor cells include AMPC and ACPC, as described herein.

As used herein, "subventricular zone" or "subventricular residuum" means a thin lamina extending inward about 50 μm from the ependymal surface, including the hippocampus alveus but excluding ependymal cells.

AMSC can be characterized as self-renewing and able to generate (i.e., differentiate into) mature, differentiated cells of the tissue type from which the cells were isolated, and the like, either in vivo, or in vitro when grown in mitogen free media. Similarly, Adult Mammalian CNS-derived Stem Cells (ACSC) can be characterized as self-renewing and able to generate (i.e., differentiate into) neurons, glia, hematopoetic cells, and the like, either in vivo, or in vitro when grown in mitogen free media.

Adult Mammalian derived Progenitor Cells (AMPC) can be characterized as self-renewing and able to generate (i.e., via replication) mature, differentiated cells of the tissue type from which the cells were isolated, and the like, either in vivo, or in vitro when grown in mitogen supplemented media. Similarly, Adult Mammalian CNS-derived Progenitor Cells (ACPC) can be characterized as self-renewing and able to generate neurons either in vivo, or in vitro when grown in mitogen supplemented media. Moreover, these ACPC are further characterized as being able to generate neurons, glia and hematopoetic cells in vitro when grown in the presence of mitogen, e.g., FGF, or the like.

Accordingly, in another embodiment of the present invention, there are provided methods for obtaining AMSC by growing AMPC in the presence of FGF-2. In one aspect of this embodiment, there is provided a method for obtaining ACSC by growing ACPC in the presence of a FGF, preferably FGF-2, 4, 6, or 8; more preferably FGF-2 or 4 and most preferably FGF-2.

For discussion purposes, as used hereinafter, "adult mammalian derived stem cells (AMSC)" includes ACSC and "adult mammalian derived progenitor cells AMPC" includes ACPC.

Invention AMSC and AMPC can be derived from any tissue, including CNS, heart, liver lung, bone marrow, and the like.

CNS tissue from which invention ACPC can be derived include whole brain, hippocampus, spinal cord, cortex, striatum, cerebellum, thalamus, hypothalamus, amigdyla, basal forebrain, ventral mesencephalon, optic nerve, locus cerleus, and the like. Indeed, it is expected that any tissue can yield progenitor and stem cells if processed in the manner described herein. In a presently preferred embodiment, invention ACSC/ACPC are isolated from the hippocampus, more preferably from the adult hippocampus.

As used herein with respect to stem cells of the present invention, "heterotypic environments" to which the cells are able to adapt include all non-source, or non-native, neural tissue such as whole brain, hippocampus, spinal cord, cortex, striatum, cerebellum, thalamus, hypothalamus, amigdyla, basal forebrain, ventral mesencephalon, optic nerve, locus ceruleus, and the like, as well as CNS associated tissues such as eye tissues, the vitreous of the eye, and the like. In addition, heterotypic environments include in vitro culture systems in which the foregoing cell types and lineages derived therefrom are cultured.

In one embodiment of the present invention, the "ability to adapt" comprises the ability of invention AMSC to respond to temporal and/or spatial cues of the heterotypic environment, either in vivo, in vitro, or both. These temporal and spatial cues include very broad classes of compounds known to have regulatory effects on cells, including those that provide differentiation signals, and the like. More particularly, as used herein, "temporal cues" refers to compounds and conditions provided by the heterotypic environment in a time-dependent manner, including development stage associated compounds, cell cycle associated compounds and conditions, as well as combinations of any two or more thereof.

As used herein, "spatial cues" include compounds and conditions provided by the heterotypic environment in a location specific manner, including any molecule or compound found in the heterotypic environment that provides cell-differentiation signals, such as trophic factors, hormones, cognate receptors for the foregoing, and the like, as well as combinations thereof.

As used herein, the term "trophic factor" refers to compounds with trophic actions that promote and/or control proliferation, differentiation, migration, survival and/or death (e.g., apoptosis) of their target cells. Such factors include cytokines, neurotrophins, growth factors, mitogens, co-factors, and the like, including epidermal growth factor, fibroblast growth factor, platelet-derived growth factor, insulin-like growth factors, ciliary neurotrophic factor and related molecules, glial-derived growth factor and related molecules, schwanoma-derived growth factor, glial growth factor, stiatal-derived neuronotrophic factor, platelet-derived growth factor, hepatocyte growth factor, scatter factor (HGF-SF), transforming growth factor-beta and related molecules, neurotransmitters, and hormones. Those of ordinary skill in the art will recognize additional trophic factors that can be employed in the present invention (see, e.g., Aebischer et al. Neurotrophic Factors (Handbook of Experimental Pharmacology, Vol 134) (Springer Verlag, 1998); Meyers, R. A. Encyclopedia of Molecular Biology and Molecular Medicine: Denaturation of DNA—Growth Factors (VCH Pub, 1996); Meager & Robinson, Growth Factors: Essential Data (John Wiley and Sons, 1999); McKay & Brown, Growth Factors and Receptors: A Practical Approach (Oxford University Press, 1998); Leroith & Bondy, Growth Factors and Cytokines in Health and Disease, Vol 1A and 1B: A Multi-Volume Treatise (JAI Pr, 1996); Lenfant et al., Growth Factors of the Vascular and Nervous Systems: Functional Characterization and Biotechnology: International Symposium on Biotechnology of Grow (S. Karger Publishing, 1992).

"Trophic factors" have a broad range of biological activities and their activity and specificity may be achieved by cooperation with other factors. Although trophic factors are generally active at extremely low concentrations, high concentrations of mitogen together with high cell density are often required to induce proliferation of multipotent neural progenitor cell populations. For example, growth factors for early progenitors may be useful for enhancing the viability of progenitor cells as well as treating disorders by renewal of mature cells from the progenitor cell pool.

Preferred trophic factors contemplated for use in the present invention are mitogenic growth factors, like fibroblast growth factor-2 (FGF-2) (Gage, F. H., et al., 1995, Proc. Natl Acad. Sci. USA 92:11879–11883) and epidermal growth factor (EGF) (Lois, C., and Alvarez-Buylla, A., 1993, Proc. Natl. Acad. Sci. USA 90(5):2074–2077), which induce proliferation and/or propogation of progenitor cells, e.g., neural progenitor cells isolated from the brain. Studies from single cells in culture demonstrate that FGF-2 (Gritti, A., et al., 1996, J. Neurosci. 16:1091–1100) and EGF (Reynolds, B. A., and Weiss, S., 1996, Develop. Biol. 175:1–13) are mitogens for multipotent neural stem cells and likely cooperate with other trophic factors (Cattaneo, E., and McKay, R., 1990, Nature 347:762–765; Stemple, D. L., and Anderson, D. J., 1992, Cell 71:973–985), some of which are yet unknown (Davis, A. A., and Temple, S., 1994, Nature 372:263–266; Temple, S., 1989, Nature 340:471–473; Kilpatrick, T. J., and Bartlett, P. F., 1993, Neuron 10:255–265; Palmer, T. D., et al., 1997, Mol. Cell. Neurosci. 8:389–404) to achieve specificity.

Hormones that provide spatial cues include thyroid hormone and the like. Receptors include the steroid/thyroid hormone superfamily of receptors, neurotrophin receptors TrkB and TrkC, and the like.

The temporal and spatial cues described herein may be provided to invention cells as either molecules that are supplied exogenously (i.e., extracellularly) or endogenously (e.g., through the expression of native and/or introduced nucleic acids encoding such molecules, and the like).

Invention AMSC are self-renewing (i.e., are capable of replication to generate additional AMSC). In addition, invention AMSC/AMPC, due to their pluripotent character, are capable of exhibiting a wide variety of responses upon exposure to a heterotypic environment with its associated temporal and spatial bio-information (i.e., cues). Because invention AMSC/AMPC are pluripotent, in one embodiment of the present invention AMSC/AMPC response to a heterotypic environment includes differentiation into a more lineage restricted type of cell found in the tissue from which the AMSC/AMPC was isolated. Accordingly, because invention ACSC/ACPC are also pluripotent stem cells, in one embodiment of the present invention, ACSC/ACPC response to a heterotypic environment includes differentiation into neurons, and glia, including astroglia and/or oligodendroglia, and the like.

As a result of the remarkable ability of invention AMSC/AMPC to adapt to a variety of heterotypic environments with the concomitant ability to integrate and differentiate, they are excellent candidates for gene therapy applications. Accordingly, in another embodiment of the present invention, there are provided AMSC/AMPC containing one or more heterologous DNA sequences (e.g., transgenes, and the like). In a presently preferred embodiment, the AMSC/AMPC are capable of expressing proteins encoded by the heterologous DNA sequences.

As described herein, invention AMSC/AMPC are able to integrate and differentiate into a number of different tissue types. Invention ACSC/ACPC are able to integrate and differentiate primarily into neural tissues. As such, invention AMSC/AMPC are useful as therapeutic agents for replacing or augmenting diseased or damaged tissue. Invention AMSC/AMPC may, however, also carry and express heterologous DNA sequences. Thus, in accordance with the present invention there are provided methods of therapy comprising administering to a patient in need thereof a cell population comprising modified AMSC/AMPC, such as, for example, those described herein, in an amount sufficient to provide a desired therapeutic effect. As those of skill in the art will understand, an amount sufficient to provide a therapeutic effect will vary according to the condition being treated, the locus of introduction, the level of enrichment for AMSC/AMPC in the donor cell population, the presence in donor AMSC/AMPC of transgenes, the relative level of expression of any such transgene(s), and the like. Accordingly, the individual practitioner may be required to take such factors into account when proceeding with a therapeutic regimen in accordance with the present invention. In one embodiment of the present invention, a therapeutically effective amount is an amount effective for introducing or complementing one or more missing and/or defective genes, wherein the gene(s) so introduced comprise heterologous genetic material contained and expresed within said AMSC/AMPC and their descendants.

Although the retina originates from the neural tube, the optic vesicle forms early in development and the retina becomes regionally isolated and highly specialized. Given this spatial and temporal separation, it would seem unlikely that ACSC/ACPC could be used to replace retinal neurons, yet these immature cells retain sufficient adaptability to integrate within the normal retina and provide a means to deliver gene products to the eye. Thus, by placing adult hippocampal stem cell and progenitors (i.e., ACSC/ACPC isolated from the adult hippocampus) into the developing and adult eye in accordance with the present invention, these cells were found to be surprisingly well suited for gene delivery. When grafted to the developing retina, adult hippocampal stem cell-progenitors (AHPCs) were broadly integrated within most layers of the retina and acquired striking morphological similarities to Müller, astroglia, bipolar, amacrine, horizontal and photoreceptor cells. Not only do these results demonstrate the considerable adaptability of adult-derived neural stem cells but also demonstrate the first successful attempt to nondestructively insert engineered normal-diploid cells into the complex architecture of the optic retina.

ACSC/ACPC are capable of reaching all layers of the retina, and differentiating into cells with local phenotypic characteristics. These cells represent an exciting new tool for studying and manipulating retinal development in mammalian species. Given that they can be propagated in vitro and, following transplantation, can extensively repopulate an actively degenerating retina in visually mature animals, this invention is also useful in treating retinal diseases involving neuronal cell loss. In view of the results discussed herein, it is expected that ACSC/ACPC will similarly be able to differentiate into the appropriate neuronal cell lineage of other neural sites into which these progenitors are transplanted in vivo. Therefore, ACSC/ACPC transplantation is also useful to treat other neurological diseases and injuries involving neuronal loss or damage. Similarly, AMSC/AMPC can be used to treat diseases and injuries to the type of tissue from which the cells were isolated.

Thus, in another embodiment of the present invention there are provided methods for the transplantation of ACPC into dystrophic neural tissue. In application, the invention encompasses a method of treating dystrophic neural tissue, comprising introducing ACPC derived from an adult animal donor into dystrophic neural tissue in an animal recipient, e.g., by grafting or applying adult progenitor cells into tissue affected by the disorder.

The recipient may be an young (immature) animal or an adult (mature) animal. The ACPC donor and recipient may be of different species (xenogeneic). Exemplary donor-recipient pairs include, but are not limited, to: a donor rat and a recipient mouse; a donor mouse and a recipient rat; a donor pig and a recipient human. The donor and recipient may be of the same species (e.g., human-to-human, rat-to-rat, mouse-to-mouse), and be allogeneic (of different strains, i.e., have different histocompatibility genes) or syngeneic (of the same strain, i.e., having identical histocompatibility genes).

Examples of dystrophic neural tissue that can be treated by the invention include the central nervous system (CNS) and neural tissue of the eye, particularly the retina or optic nerve. Thus, in another embodiment, the invention encompasses a method of repopulating or rescuing a dystrophic retina with neural cells, comprising introducing neural progenitor cells derived from an adult donor (e.g., ACPC or ACSC) into dystrophic neural tissue of an animal recipient. The method is particularly useful for treating dystrophic retinal tissue caused by an optic neuropathy, e.g., glaucoma.

As used herein, the term "dystrophic neural tissue" encompasses damaged, injured, or diseased neural tissue, which neutral tissue includes differentiated neural tissue. Thus the present invention provides methods for treating a neuronal or neural disorder or neural injury. A "neuronal disorder" or "neural disorder" is any disorder or disease that involves the nervous system. One type of neuronal disorder is a neurodegenerative disorder. Neurodegenerative disorders include but are not limited to: (1) diseases of central motor systems including degenerative conditions affecting the basal ganglia (e.g., Huntington's disease, Wilson's disease, Striatonigral degeneration, corticobasal ganglionic degeneration, Tourettes syndrome, Parkinson's disease, progressive supranuclear palsy, progressive bulbar palsy, familial spastic paraplegia, spinomuscular atrophy, ALS and variants thereof, dentatorubral atrophy, olivopontocerebellar atrophy, paraneoplastic cerebellar degeneration, cerebral angiopathy (both hereditary and sporadic)); (2) diseases affecting sensory neurons (e.g., Friedreich's ataxia, diabetes, peripheral neuropathy, retinal neuronal degeneration); (3) diseases of limbic and cortical systems (e.g., s cerebral amyloidosis, Pick's atrophy, Retts syndrome; (4) neurodegenerative pathologies involving multiple neuronal systems and/or brainstem (e.g., Alzheimer's disease, AIDS-related dementia, Leigh's disease, diffuse Lewy body disease, epilepsy, Multiple system atrophy, Guillain-Barre syndrome, lysosomal storage disorders such as lipofuscinosis, late-degenerative stages of Down's syndrome, Alper's disease, vertigo as result of CNS degeneration; (5) pathologies arising with aging and chronic alcohol or drug abuse (e.g., with alcoholism the degeneration of neurons in locus oeruleus, cerebellum, cholinergic basal forebrain; with aging degeneration of cerebellar neurons and conical neurons leading to cognitive and motor impairments; and with chronic amphetamine abuse degeneration of basal ganglia neurons leading to motor impairments; and (6) pathological changes resulting from focal trauma such as stroke, focal ischemia, vascular insufficiency, hypoxic-ischemic encephalopathy, hyperglycemia, hypoglycemia or direct trauma.

The presence of a neuronal or neurodegenerative disorder or injury may be indicated by subjective symptoms, such as pain, change in sensation including decreased sensation, muscle weakness, coordination problems, imbalance, neurasthenia, malaise, decreased reaction times, tremors, confusion, poor memory, uncontrollable movement, lack of affect, obsessive/compulsive behavior, aphasia, agnosia, visual neglect, etc. Frequently, objective indicia, or signs observable by a physician or a health care provider, overlap with subjective indicia. Examples of objective indicia include the physician's observation of signs such as decreased reaction time, muscle fasciculations, tremors, rigidity, spasticity, muscle weakness, poor coordination, disorientation, dysphasia, dysarthria, and imbalance. Additionally, objective signs can include laboratory parameters, such as the assessment of neural tissue loss and function by Positron Emission Tomography (PET) or functional Magnetic Resonance Imaging MRI), blood tests, biopsies and electrical studies such as electromyographic data.

"Treating" dystrophic neural tissue is intended to encompass repairing, replacing, augmenting, rescuing, or repopulating the diseased or damaged neural tissue, or otherwise compensating for the dystrophic condition of the neural tissue.

"Introduction" of ACPC/ACMC or ACSC/ACPC into dystrophic neural tissue (e.g., a damaged or diseased retina or optic nerve), may be accomplished by any means known in the medical arts, including but not limited to grafting and injection. It should be understood that such means of introducing the neural progenitor cells also encompass placing, injecting or grafting them into a site separate and/or apart from the diseased or damaged neural tissue site, since the neural progenitor cells are capable of migrating to and integrating into that dystrophic site. For example, dystrophic retinal or optic nerve tissue can be treated by placing neural progenitor cells into the vitreous of the eye.

In another aspect of the foregoing embodiment of the present invention, there are provided therapeutic methods comprising administering to a patient in need thereof an amount of ACSC/ACPC effective to repair or replace defective, damaged or dead tissue. In a presently preferred embodiment, cells which are to be added to or replaced comprise optic cells, including, retinal cells, Müller cells, amacrine cells, bipolar cells, horizontal cells, photoreceptors, astroglial cells, and the like.

Because of the pluripotent nature of invention AMSC/AMPC, and the resulting multiplicity of loci where such cells may be introduced in order to achieve therapeutic effects, there is a broad range of tissue damage and disease states which can be treated using invention AMSC/AMPC. Many disease states (e.g., liver disease) result in damaged or necrotic tissue. These types of diseases are ideal for replacement or augmentation therapy comprising the administration of invention AMSC/AMPC. The plastic and pluripotent nature of AMSC/AMPC make them ideal candidates for their use as a source of cells which can be used to replace or correct for cells lost in disease or injury, even in the absence of exogenous genetic material. For example, invention AMSC/AMPC can be used to replace a variety of tissue types throughout the body that are encompassed within the different phenotypes that progeny of AMSC/AMPC can exhibit, upon differentiation, including glial cells, neurons, and the like. Accordingly, in a particular embodiment of the present invention, there are provided therapeutic methods comprising administering to a patient in need thereof a cell population comprising AMSC/AMPC as described herein, in an amount sufficient to provide a therapeutic effect. In one aspect of the present invention, expression of AMSC/AMPC native genes in the cell population occurs as necessary for AMSC/AMPC to proliferate and differentiate in order to replace or add cells of a desired type.

The therapeutic benefit of the invention can be evaluated or assessed by any of a number of subjective or objective factors indicating a response of the condition being treated. Such indices include measures of increased neural or neuronal proliferation or more normal function of surviving brain areas. In addition, macroscopic methods of evaluating the effects of the invention can be used which may be invasive or noninvasive. Further examples of evidence of a therapeutic benefit include clinical evaluations of cognitive functions including object identification, increased performance speed of defined tasks as compared to pretreatment performance speeds, and nerve conduction velocity studies.

In another aspect of the invention, the neural progenitor cells have preferably been cultured in vitro in a culture medium comprising at least one trophic factor, or even combinations of such factors.

As used herein, the neural progenitor cells can be cultivated in the presence of a trophic factor, or combinations of trophic factors. For example, these cells can be cultivated in medium having "neurotrophins" (or "neurotrophic factor") that promote the survival and functional activity of nerve or glial cells, including a factor that enhances neural differentiation, induces neural proliferation, influences synaptic functions, and/or promotes the survival of neurons that are normally destined to die, during different phases of the development of the central and peripheral nervous system. Exemplary neurotrophins include, for example, ciliary neurotrophic factor (CNF), nerve growth factor (NGF), fibroblast growth factor (FGF), brain-derived neurotrophic factor (BDNF), Neurotrophin-3 (NT-3), glia derived neurotrophic factor (GDNF), and the like. Such factors are characterized by their trophic actions, their expression patterns in the brain, and molecular aspects of their receptors and intracellular signaling pathways. Neurotrophic factors that have been identified include NT4, NT-5, NT-6, NT-7, ciliary neuronotrophic factor (CNTF), Glial cell line-derived neurotrophic factor (GDNF), and Purpurin. Neuron-specific enolase (NSE) has been found to be a neuronal survival factor. Other factors possessing a broader spectrum of functions, which have neurotrophic activities but are not normally classified as neurotrophins, also are contemplated for use in the invention. These "neurotrophin-like factors" include epithelial growth factor (EGF), heparin-binding neurite-promoting factor (HBNF), IGF-2, a-FGF and b-FGF, PDGF, neuron-specific enolase (NSE), and Activin A. Other factors have been identified which specifically influence neuronal differentiation and influence transmitter phenotypes without affecting neuronal survival. Although the intracerebral administration of FGF-2 has been shown to stimulate neurogenesis in the adult rat SVZ, FGF-2 alone in the adult rat hippocampus has a limited effect on the proliferation of neural stem/progenitor cells (Kuhn et al. (1997); Wagner et al. (1999) each herein incorporated by reference).

In a preferred embodiment of the present, the present invention employs FGF and FGF-like factors, including a-FGF, b-FGF such as FGF-2, FGF4, FGF6, and the like. A particularly advantageous medium for culturing neural progenitor cells comprises one of the following: fibroblast growth factor (FGF) alone (particularly basic FGF or FGF-2), FGF plus epidermal growth factor (EGF), or FGF plus EGF plus heparin, which is mitogenic.

In view of the foregoing observations, and in view of the observation that many tissues have latent poppulations of progenitor and/or stem cells, in another embodiment of the present invention, there are provided methods for inducing the proliferation and differentiation of stem and progenitor cells in situ. Thus, in one aspect of this embodiment, a therapeutically effective amount of agent comprising one or more of a neurotrophic factor (i.e., nuerotrophin), a mitogen, a neuotrophin-like factor, or the like is administered to a subject with damaged, diseased or dystrophic tissue (e.g., neuronal tissue such as retina, or the like). It is presently preferred that the agent be directly administered to the affected tissue via injection, topical application, or the like.

Some disease states are characterized by one or more defective or missing genes. Such diseases are ideally treated by the adminstration of invention AMSC/AMPC containing one or more transgenes. Thus, in another embodiment of the present invention, there are provided therapeutic methods as described herein, wherein one or more disease associated transgenes incorporated and expressed in said invention AMSC/AMPC. Examples of neuronal tissue-associated disease states and their associated genes include Huntingtons Corea (one or more of gamma amino butyric acid (GABA) decarboxyalse and ciliary neurotrophic factor (CNTF)), Alzheimer's disease (one or more of acetylcholinesterase, neuronal growth factor (NGF), brain derived neurotrophic factor (BDNF) and fibroblast growth factor (FGF)), Parkinson's disease (one or more of tyrosine hydroxylase, DOPA decarboxylase, DMAT, GDNF, BDNF and FGF), amyotropic lateral sclerosis (CNTF), and the like.

While invention AMSC/AMPC are useful to introduce therapeutic genes, it may be desirable to introduce into a host or patient one or more genes that are not strictly therapeutic but which may be useful in other ways, for example, as tracking genes (i.e., markers), as genes to induce migration, as genes to induce mitosis, as survival genes, as suicide genes, and the like. Marker genes contemplated for use in the practice of the present invention include genes encoding a modified green fluorescent protein (GFP) derived from jellyfish, β-Galatosidase (the LacZ gene product), neomycin phosphotransferase (neo), Luciferase, and the like.

As will be recognized by those of skill in the art, a variety of methods exist for the introduction of genetic material into cells such as invention AMSC/AMPC. Such methods include viral and non-viral methods. Non-viral methods contemplated for use in the practice of the present invention include electroporation, microinjection, polyethylene glycol precipitation, high velocity ballistic penetration by small particles with the nucleic acid to be introduced contained either within the matrix of such particles, or on the surface thereof (Klein, el al., *Nature* 327:70, 1987), or the like. Viral methods contemplated for use in the practice of the present invention include the use of retroviral vectors, and the like. It is presently preferred that retroviral vectors be employed for introducing genetic material into invention AMSC/AMPC. In one aspect of the present invention, replication deficient vectors are employed. Such vectors are well known to those of skill in the art.

Numerous examples of disease exist that are suitable for treatment with invention AMSC/AMPC. Some of these disease states are equally suited for treatment using invention AMSC/AMPC with and/or without incorporated transgenes. For example, the liver plays a central role in the pathophysiology of many inherited metabolic diseases. Although the adult liver has the unusual ability to regenerate after injury, the liver is an important target for cell therapy. Therefor, in another embodiment of the present invention AMSC/AMPC are introduced into the liver where they differentiate into hepatocytes, and replace dead and dying cells, thereby correcting disease phenotypes. When particular diseases are associated with one or more missing or defective genes, such diseases are treatable with invention AMSC/AMPC wherein the missing/defective gene(s) is/are incorporated.

Recent experimental data from immune and endocrine studies using spontaneous or transgenic models of diabetes have emphasized the role of islets of Langerhans, and particularly beta cells, in autoimmune insulin-dependent (Type 1) diabetes mellitus (IDDM) pathogenesis. IDDM is a chronic disorder that results from the destruction of the insulin-producing beta cells of the pancreatic islets. Accordingly, in another aspect of the present invention, AMSC/AMPC can be grafted in the pancreas for the replacement of damaged pancreas cells with the grafted cells. When particular diabetic pathologies are associated with one or more missing or defective genes, such pathologies are treatable with invention AMSC/AMPC wherein the missing/defective gene(s) is/are incorporated.

Duchenne muscular dystrophy (DMD) is characterized by slow and progressive muscle weakness affecting limb and respiratory muscles, which degenerate until fatal cardiorespiratory failure. Myodystrophy of the Duchenne type results from mutations affecting the gene for dystrophin, a cytoskeletal protein. A form of congenital dystrophy caused by a deficiency of the a2 subunit of the basement membrane protein laminin/merosin is termed Merosin-Deficient Congenital Muscular Dystrophy (MCMD). Accordingly, in another aspect of the present invention, AMSC/AMPC are grafted into muscles wherein they differentiate to become myoblasts and replace degenerating muscle cells.

Cardiac disease, typified in many instances by damaged heart muscle, is another target for cell replacement. Accordingly, in yet another aspect of the present invention, AMSC/AMPC are transplanted into the heart to replace diseased cells and improve heart function.

Pulmonary disease (i.e., Cystic fibrosis) is the most common autosomally inherited disease, and is caused by the defective gene Cftr, which encodes an ion channel at the cell membrane. Augmentation of lung tissue with AMSC/AMPC can alleviate the reduced respiratory function caused by the defective genotype. Accordingly, in still another aspect of the present invention, AMSC/AMPC are grafted into the lung in order to replace the diseased cells having defective ion channels, and restore normal lung function. As a heritable disorder, this disease is also an ideal candidate for treatment using invention ACSC/ACPC with appropriately incorporated Cftr-augmenting exogenous nucleic acids.

As readily understood by those of skill in the art, the most direct method for administration of invention AMSC/AMPC to the desired site is likely to be by injection, however, any means of administering cells that results in correct localization and integration is contemplated for use in the practice of the present invention.

As those of skill in the art will understand, a number of factors may be determinative of when and how a stem or progenitor cell differentiates. As a result, it may be desirable to induce differentiation of invention AMSC/AMPC in a controlled manner and/or by employing factors which are not easily or desirably introduced into the locus of therapeutic AMSC/AMPC introduction. Accordingly, in another embodiment of the present invention, there are provided therapeutic methods as described herein, wherein said AMSC/AMPC have been induced to differentiate, prior to administration to the subject, by in vitro exposure to extracellular and/or intracellular factors described herein, including trophic factors, cytokines, mitogens, hormones, cognate receptors for the foregoing, and the like, as well as combinations of any two or more thereof.

As will be appreciated by those of skill in the art, proper isolation and treatment of source tissues for AMSC/AMPC is desirable in order to obtain a population of cells comprising AMSC/AMPC. ACSC/ACPC are used as a paradigm for the present disclosure, however, any tissue type may be employed to isolate corresponding AMSC/AMPC. Thus, while a whole brain or other source neuronal tissue, as described herein, all comprise ACSC/ACPC, it is desirable for therapeutic purposes to provide a cell population containing primarily ACSC/ACPC and lacking a substantial amount of other cell types and/or debris. Accordingly, it is presently preferred that cell populations be enriched for ACSC/ACPC. This enrichment can be carried out by a number of methods. Thus, in accordance with one embodiment of the present invention there are provided methods for enriching a cell population containing adult mammalian CNS tissue for adult mammalian CNS-derived stem cells (ACSC), said method comprising subjecting dissociated mammalian CNS tissue to one or more separation systems. Although it is contemplated that, with proper execution, any separation system can be adapted to isolate ACSC/ACPC from CNS tissue, separation systems contemplated for use in the practice of the present invention include buoyancy-based separation systems, charge-based separation systems, fluorescent activated cell sorting systems (FACS), and the like, as well as combinations thereof.

It is presently preferred that buoyancy based separation systems be employed in the practice of the present invention. In one embodiment of the present invention, the buoyancy based separation system employed is density gradient centrifugation. Density gradients can be crated using any suitable media, including, PERCOLL™ (polyvinylpyrrolidone-coated silica colloids), FICOLL™ (copolymers of sucrose and epichlorohydrin), sucrose, and the like. In an even more preferred embodiment of the present invention, a PERCOLL™ (polyvinylpyrrolidone-coated silica colloids) gradient is employed. Invention AMSC/AMPC will typically have a density in the range of about 1.06 up to about 1.08 g/ml; and more typically a density in the range of about 1.072 up to about 1.075 g/ml. Thus, in a presently preferred embodiment of the present invention, the PERCOLL™ (polyvinylpyrrolidone-coated silica colloids) gradient employed in the practice of the present invention is an approximately 50% PERCOLL™ (polyvinylpyrrolidone-coated silica colloids) gradient. As will be understood by those of skill in the art, the gradient can be modified to take into account the buoyant density of the particular stem cells being sought (e.g., hepatic stem cells, or the like).

The invention will now be described in greater detail by referring to the following non-limiting examples.

EXAMPLES

Example 1

Isolation of Multipotent CNS Progenitor Cells from Adult Rodent Brain Via PERCOLL™ (polyvinylpyrrolidone-coated Silica Colloids) Density Gradient Centrifugation This example demonstrates that ACSC/ACPC can be isolated from whole adult brains via density gradient centrifugation.

Gradient Calibration. In order to derive the preferred gradient conditions for isolating ACSC/ACPC, established adult hippocampal progenitor cells were harvested from culture dishes by trypsinization and a cell suspension was obtained by suspending the trypsinized cells in 65% conditioned medium, 35% PERCOLL™ (polyvinylpyrrolidone-coated silica colloids). The gradients were initially prepared by mixing various ratios of PERCOLL™ (polyvinylpyrrolidone-coated silica colloids) to conditioned media in 14×89 mm Ultra-Clear polycarbonate centrifuge tubes (Beckman). Dilutions of 90%, 80%, 70%, 60%, and 50% were made. 1 ml of the cell suspension was applied as a "stacker" solution to the top of each of these dilutions of PERCOLL™ (polyvinylpyrrolidone-coated silica colloids). After centrifugation, the gradients were divided into four equal fractions. The factions were collected by aspirating from the top with a P-1000 pipetteman (Gilson). The fractions were then washed twice in 5 volumes of PBS and replated onto PORN-LAM coated dishes in DMEM F12+ bFGF.

Dissection. Adult female Fischer 344 rats (4–6 months of age) were anesthetized with a mixture of ketamine (44 mg/kg), acepromazine (0.75 mg/kg), and xylazine (4 mg/kg) in 0.9% NaCl and decapitated. The brains were removed and placed into cold phosphate-buffered saline (PBS).

Tissue Preparation. A cell suspension was obtained by pooling the brains from 6 animals from which the cerebella had been trimmed away. The remaining brain tissue was then weighed. The brains were diced into small fragments, and then digested for 40–50 min at 37° C. in Hanks' balanced salt solution containing 0.1% grade II neutral protease (Boehringer Mannheim), 0.01% papain (Worthington), and 0.01% Dnase I (Worthington). The mixture was shaken every five minutes. Every fifteen minutes during the digestion, the tissues were gently disrupted by pipetting the digestion reaction mixture through a 5-ml pipette. The tissue was then rinsed two times with DMEM/F12 containing 10% fibroblast bovine serum, to inactivate digestive enzymes, and filtered through nylon mesh (Nitex, 100 μm pore size), to remove undissociated tissue. The filtered cells were resuspended to a final volume of 10 ml in DMEM/F12/10% FBS.

PERCOLL™ (polyvinylpyrrolidone-coated silica colloids) density gradient preparation and centrifugation. 100% isotonic PERCOLL# (polyvinylpyrrolidone-coated silica colloids) (Pharmacia) solutions (300 mOsm/kg $H_2O$ (Enerbäck 1980)) were prepared by dissolving 9 parts of PERCOLL™ (polyvinylpyrrolidone-coated silica colloids) with 1 part of 10-fold concentrated PBS. 5 ml of this 100% PERCOLL™ (polyvinylpyrrolidone-coated silica colloids) solution were added to each of two 14×89 mm Ultra-Clear polycarbonate centrifuge tubes (Beckman) which were pre-sterilized with ethylene dioxide gas. To each tube, 5 ml of the cell suspension was added and mixed together with the PERCOLL™ (polyvinylpyrrolidone-coated silica colloids). This yields a 50% PERCOLL™ (polyvinylpyrrolidone-coated silica colloids) mixture. A Beckman L8-80M preparative ultracentrifuge was used for centrifugation. Continuous density gradients of PERCOLL™ (polyvinylpyrrolidone-coated silica colloids) were generated by centrifugation at 20,000×g for 30 min in a Beckman SW-41 Ti swinging bucket rotor. All centrifugations were performed at 25 C.

After centrifugation, the gradients were divided into four equal fractions. The fractions were removed by inserting a syringe with a 22 gauge ½ inch needle into the side of each tube and collecting the fractions, starting from the bottom. The needle was inserted near the bottom of the tube with the bevel facing upwards, just above a band of red blood cells which is consistently generated during the centrifugation. The lower fractions and the upper fractions, respectively, were pooled and rinsed twice in 5 vol of PBS to remove PERCOLL™ (polyvinylpyrrolidone-coated silica colloids) from the cells. Cells were the resuspended in Dulbeoco's Modified Eagle's Medium/Ham's F12 (DMEM/F12, 1:1) supplemented with 10% defined fibroblast bovine serum (FBS, Hyclone) and plated into 4 polyomithine/laminin-coated 6 cm dishes (Falcon), two for the upper fractions and two for the lower fractions. On the following day, the medium was removed and replaced with fresh DMEM/F12 containing N2 supplement (Gibco) and 20 ng/ml FGF-2 (provided by A. Baird). The medium removed from the initial plating was centrifuged in a tabletop clinical centrifuge in order to recover any cells that had not yet adhered to the culture dishes. These cells were put back into their respective culture dishes after the supernatant was discarded. Every other day, the cells were "passaged" by removing half of the media and replacing it with fresh N2-containing medium supplemented with 20 ng/ml FGF-2. The cells from the lower fraction reached confluency after 7 days and were subsequently passaged every 4–6 days.

Cells isolated in accordance with the foregoing method were observed to be inducible to proliferate by in vtro treatment with 20 ng/ml bFGF as do established progenitor cells. Similarly, it was observed that PERCOLL™ (polyvinylpyrrolidone-coated silica colloids) isolated cells exhibited virtually the same immunostaining, and thus the same pattern of antigen expression, as established progenitor cells when challenged with a panel of antibodies reactive for maturity stage specific CNS cell markers, including A2B5, Nestin, Map2abc, Vimentin, Tuj1, Map5, NCAM, NSE, NeuN, NF200, Tau, and O4. Notably, however, the established progenitor cells were reactive for Map2abc (an immature CNS marker) yet the PERCOLL™ (polyvinylpyrrolidone-coated silica colloids) isolated cells were not. Cells isolated by the forgoing method were also tested for multipoteny. It was observed that exposing PERCOLL™ (polyvinylpyrrolidone-coated silica colloids) colloids) isolated cells to conditions known to favor differentiation of CNS progenitors also led to selective differentiation of PERCOLL™ (polyvinylpyrrolidone-coated silica colloids) isolated cells. Thus, the forgoing example indicates that progenitor cells can successfully be isolated using PERCOLL™ (polyvinylpyrrolidone-coated silica colloids) gradient density centrifugation, with the resulting cells indicating the patterns of protein expression and response to differentiation inducing conditions as known progenitor cells.

Example 2

Second Method for Isolation of Multipotent CNS Progenitor Cells From Adult Rodent Brain Via PERCOLL™ (Polyvinylpyrrolidone-coated Silica Colloids) Density Gradient Centrifugation Tissue dissection: Three areas were dissected from adult rat brains as follows. Rats (170–190 g Fisher 344 males or females, Harlan) were deeply anesthetized with a mixture of ketamine, xylazine, and acepromazine. Animals were decapitated and whole brains removed. First, ~1.5 mm of each optic nerve were harvested rostral to, but not including, the optic chiasma. The brain was then bisected longitudinally and each hippocampal lobe separated from the overlaying cortical white matter using the natural separation line along the alveus hippocampus. The white matter of the fimbria and subiculum was removed as much as possible. Some white matter remained. Finally, a 1.5 mm wide cortical ribbon containing parietal and frontal segments was dissected longitudinally, proximal to the central fissure. The pial and callosal surfaces were trimmed from each cortical ribbon to remove a majority of the meninges and white matter.

Tissue dissociation and fractionation: Tissues were finely minced and digested in a solution of papain (2.5 U/ml, Worthington), DNAse (250 U/ml, Worthington), and neutral protease (1 U/ml Dispase, Boehringer) dissolved in Hanks balanced salt solution, as described in Palmer T D, Ray J, Gage F H (1995), FGF-2-Responsive Neuronal Progenitors Reside in Proliferative and Quiescent Regions of the Adult Rodent Brain. *Mol Cell Neurosci* 6:474–486; and Gage F H, Coates P W, Palmer T D, Kuhn H G, Fisher L J, Suhonen J O, Peterson D A, Suhr S T, Ray J (1995), Survival and differentiation of adult neuronal progenitor cells transplanted to the adult brain. *Proc Natl Acad Sci USA* 92:11879–11883. Cells and tissue fragments were washed 3 times with Dulbecco's Modified Eagles Medium (DMEM) containing 10% fibroblast bovine serum (defined FBS, Hyclone). Whole digested tissue was then suspended in DMEM 10% FBS, filtered through a sterile 107 μm nylon mesh and thoroughly mixed with an equal volume of PER- COLL™ (polyvinylpyrrolidone-coated silica colloids) solution. The PERCOLL™ (polyvinylpyrrolidone-coated silica colloids) solution was made by mixing 9 parts of PERCOLL™ (polyvinylpyrrolidone-coated silica colloids) (Pharmacia) with 1 part 10X phosphate buffered saline (PBS, Irvine Scientific). The cell suspension was then fractionated by centrifugation for 30 minute, 18°C., at 20,000×g. Cell fractions wee harvested and washed free of PERCOLL™ (polyvinylpyrrolidone-coated silica colloids) by 3 or more rinses in DMEM, 10% FBS.

Cell culture: PERCOLL™ (polyvinylpyrrolidone-coated silica colloids) gradients were optimized using perpetualized hippocampal stem cell clones, AP31 and PZ5a. (Palmer T D, Takahashi J. Gage F H (1997) The adult rat hippocampus contains primordial neural stem cells. *Mol Cell Neurosci* 8:389–404). These cultures are stem cell-derived and contain a mixture of lineages at various stages of differentiation. The most immature cells had remarkably high densities ranging from 1.065 to 1.075 g/ml. On the assumption that the most immature cells within the adult brain would have similarly high densities, the gradients were optimized using beads of known densities to generate step density profiles spanning 1.060 to 1.075 g/ml. All cells with densities lower than 1.060 g/ml were expected to form a band at the top of the gent whereas those with a buoyancy similar to the immature cultured progenitors would migrate into the gradient. Stem-like cells in perpetualized cultures typically formed a discrete band at the bottom of the gradient.

Bromodeoxy uridine (BrdU) labeling was first used to mark endogenously proliferating cells for identification in situ. Adult rats were injected with BrdU once each day for 6 consecutive days and then brains were collected for evaluation on day 7. Two percent of all labeled nuclei within the hippocampus were found within the putative subventricular residuum. Ependymal cells proper accounted for 4% of the total labeled population and a similarly small proportion was found within the neurogenic zone of the SGZ (8%). In contrast, 52% were present in the white matter of the fimbrial ridge, and the remainder were scattered throughout the parenchyma. A similar comparison of neocortical gray and white matter showed that 15% of the BrdU-labeled cells were present in the parenchyma of the cortex. The remaining 85% were present in the subcortical white matter and associated SVZ.

To determine if endogenously proliferating progenitors could be isolated from adult tissue on the basis of buoyant density, adult rats were injected with BrdU 4 times over a 48-hour period. Whole hippocampal lobes or cortical ribbons were dissociated and fractionated over PERCOLL™ (polyvinylpyrrolidone-coated silica colloids) gradients. Three visible bands of cells were formed. A layer of red blood cells (RBCs) formed near the bottom of the gradient. A band of nucleated cells with buoyant densities similar to those of cultured progenitors formed just above the RBC layer and a majority of the remaining differentiated cells, as well as tissue fragments and myelinated neuropil, formed a large band at the top of the gradient. A small number of cells were diffusely distributed throughout the gradient. Hippocampal tissues yielded 1015 +/− 31 cells per mg tissue in the lower band and cortical tissues yielded 732 +/− 24 cells per mg of tissue (mean +/− s.e.m, n=5).

Cells from the upper and lower region of each gradient were collected. A fraction of each population was immediately fixed and evaluated for BrdU and lineage-specific markers. The upper fractions were so contaminated with cell debris and myelin that it was very difficult to determine phenotype with the exception of BrdU immunoreactivity in cell nuclei. For both hippocampal (HC) and cortical tissues, there were very few BrdU-labeled cells in the high buoyancy fraction (<1 cell detected in 5000 nuclei scored for both HC and cortex) and the few cells not trapped within aggregates of debris nearly all expressed neuronal or glial markers. BrdU-labeled cells were found predominantly in the lower band, with 0.7% or 0.1% of all hippocampal or cortical cells labeled. In both hippocampal and cortical preparations, <0.1% of the low buoyancy cells were glial fibrillary acidic protein (GFAP) immunoreactive astrocytes. Although a few immature neurons (β Tubulin) were present in the hippocampal population (0.1%), none were detected in the low buoyancy cortical fraction. A significant fraction of cells were immunoreactive for vimentin (37% and 35% in hippocampus and cortex, respectively) and vimentin expression was rapidly upregulated with 87% and 89% of all cells expressing vimentin after 36 hours in culture. Vimentin, a marker attributed to ependymal cells, immature astrocytes and radial glia, is also known to be expressed by multipotent precursors in perpetualized neural precursor cultures. Some cells in both fresh and 36-hour populations were weakly immunoreactive for O4, a marker first attributed to immature oligodendrocytes and also expressed by FGF-2 stimulated multipotent precursors in vitro. Nestin, a marker for immature precursors, was detected in 15% or 7% of the freshly isolated cells from HC or cortex, respectively, but was then transiently downregulated. At 36 hours in culture, very few cells expressed detectable nestin, yet one week later, virtually all cells in both hippocampal and cortical cultures were nestin-positive.

The quality of the vimentin staining in the low buoyancy fraction also proved to be informative. After 36 hours in culture, vimentin staining was intense in cells with a flattened, neurepithelial-like morphology and weak in phase bright cells reminiscent of progenitors in long-term cultures. Upon acid pretreatment (required for the immunological detection of BrdU), only the intensely staining cells remained immunoreactive. This staining pattern was also seen in vivo where the acid-stable vimentin immunoreactivity was restricted to the ependyma proper, whereas glia in the parenchyma exhibited a weaker, acid-labile staining. In addition, some of the cells in the low buoyancy fraction were motile during the first few hours of culture. When stained with Coomassie blue, many of the vimentin-positive cells had easily detectable cilia typical of ependymal cells and a small portion of cells were motile within the freshly isolated lower fraction. On the basis of acid-stable vimentin staining, as many as 30% to 35% of the cells in low buoyancy fraction from both HC and cortex may have been ependymal cells.

Although BrdU-labeled cells fractionated to the low buoyancy population, most of the isolated cells were unlabeled, consistent with the isolation of immature, yet relatively quiescent precursors. To determine if the unlabeled cells were competent to proliferate or simply lineage marker-negative terminally differentiated cells, hippocampus or cortex was fractionated and cells from the low buoyancy fraction cultured in defined medium containing 20 ng/ml FGF-2 (DMEM/F12 containing N2 supplement and 20 ng/ml FGF-2, "growth medium"). Cell division was monitored by counting cells and by treating replicate cultures with BrdU at different times post plating. Following a delay of several days, cells began an exponential growth pattern that reached a steady state in 7 to 10 days. After 10 days, growth rates were similar to those of the perpetualized cultures with roughly 85% of the cells dividing in a given 24-hour period and >99% of the cells labeled following a 48 hour exposure to BrdU.

The freshly isolated cells also displayed a density dependent growth that was similar to that seen in perpetualized stem cell cultures. Plating densities of ~10,000 cells/cm2 or higher were required for optimum proliferation whereas cells plated at clonal densities (<1 cell/cm2) grew very slowly or not at all. By fractionating cells, not only was it possible to eliminate debris and differentiated cells, but those cells remaining could be plated immediately into culture at densities that promoted the recruitment of cells into cycle.

Example 3

Demonstration of the Lineage Potential of Cells Isolated by Invention Methods

The lineage potential of progenitors from cortex or hippocampus was determined by culturing low buoyancy cells (isolated per Example 2) in growth medium for 14 days and then allowing cells to differentiate under conditions known to stimulate both neuronal and glial differentiation (differentiation medium: 1 ng/ml FGF-2, 1% fibroblast bovine serum, and 100 nM all-trans retinoic acid). Culture conditions were as set forth in Example 2. At 14 days, few of the cells expressed markers for neurons or glia. Of the total population in HC or cortical cultures, 0.8% or 0.2%, respectively, were immunoreactive for β Tubulin (neurons), 1.1% or 1.7% were immunoreactive for GFAP (astrocytes) and 24% or 25% were immunoreactive for O4, a marker often attributed to immature oligodendrocytes, but also expressed by multipotent progenitors in long term FGF-2 stimulated cultures. There were no GalC-positive oligodendrocytes (<0.01%) detected in either culture. Following differentiation for 7 days, both cultures contained numerous cells from all three lineages. Cortical cultures tended to contain a higher proportion of astrocytes (36% vs. 28% for the hippocampus). Both hippocampal and cortical cultures contained similar numbers of highly arborized oligodendrocytes (1% and 2%, respectively) and each contained significant numbers of neurons (8% and 3%, respectively).

To determine if the neurons in the cortical populations were derived from proliferative multipotent precursors, retroviral marking was used to evaluate the lineage potential of cells within the low buoyancy fractions. Cells were first stimulated with FGF-2 for 7 days to induce proliferation (a prerequisite for retroviral infection) and then retroviruses carrying a green fluorescent protein (GFP) transgenes were used to infect the proliferating population. Individual infected cells were marked and allowed to proliferate within the non-infected bulk population for an additional 7 days. The resulting colonies were then induced to differentiate in differentiation medium. A typical population of colonies was generated using an excess of virus (multiplicity of infection, m.o.i. ~0.01). To avoid overlapping colonies, roughly 50 infectious units (iu) were used in each assay below (m.o.i. ~$10^{-4}$). The number of colonies generated per 10 cm assay dish ranged from 4 to 21. To determine if individual colonies were indeed clonal, the positions of individual marked cells were documented 24 to 36 hours after infection and then colony growth was monitored daily. The incidence of closely juxtaposed cells giving rise to overlapping colonies with such low virus concentrations was insignificant (two clones were excluded in 543 clones scored). The remaining quantitation was performed as a "colony assay" on the assumption that all colonies separated by a centimeter or more were derived from single cells.

Clones were grouped into five categories based on the expression of lineage-specific markers and morphology. Neuron-only clones were infrequent (5.3%) in the hippocampal preparations and rare (<0.1%) in cortex-derived cultures. Some clones were glial-restricted and contained only GFAP-positive astrocytes and/or O4-positive oligodendrocytes. A small but significant proportion of the marked cells (21% and 17% from hippocampus and cortex, respectively) produced a mixture of glia and neurons. The remaining clones were negative for all three lineage markers. The marker-negative cells were further divided into two clone types; one type was very large and consisted of flattened, phase dark cells strongly immunoreactive for the acid stable vimentin epitope. The remaining marker-negative clones were small and contained large bipolar cells with simple, large caliber processes.

When scored by size, neuron-only clones contained few cells whereas glial-restricted progenitors and multipotent progenitors generated colonies of intermediate size. The largest clones were the lineage marker-negative, vimentin-positive clones. Although the large size may suggest a faster growth rate in the 7 days following infection, it was determined that this large size was an artifact caused by continued growth in differentiation medium. When observed during the first 7 days after viral infection, the clones with the flattened phase dark morphology typical of these large lineage negative clones actually grew more slowly than the other clones being monitored. Continued growth in differentiation medium was confirmed by repeating these experiments in the presence of BrdU during differentiation. The large marker-negative clones were uniformly labeled with BrdU whereas cells from the smaller neuron-only, glia-only, or mixed clones were unlabeled.

The clonal analysis demonstrated that roughly half of the lower fraction of cells from both cortex and hippocampus was made up of cells that formed large colonies but did not differentiate into neurons or glia. Though the acid-stable vimentin staining in these cells is consistent with an ependymal origin, the lineage of these cells has not been determined. The remaining cells consisted of neural progenitors of mixed lineage potential. Approximately 20% of all cells isolated were able to generate both neuronal and glial progeny, indicating that both cortex and hippocampus contained multipotent precursors.

Example 4

FGF-2 Stimulates Neurogenesis

Neurogenesis is not detected in the adult cortex yet a significant number of the progenitors from cortical tissues were competent to generate neurons once removed from their in vivo environment. Activation of this neurogenic program could be triggered by several mechanisms. One possibility is that multipotent precursors may yield progeny that are competent to differentiate into neurons but are suppressed by cell extrinsic signals in vivo. If so, the simple act of removing them from the in vivo environment may disinhibit or activate a latent neuronal differentiation program. To test this possibility, low-buoyancy cells were isolated from adult tissue and immediately plated into differentiation medium as described above. The presence of β Tubulin-positive neurons was scored after 10 days. Both cortical and hippocampal populations generated abundant populations of glia but only the hippocampal preparations generated β Tubulin-positive neurons. The absence of neurons in cortical preparations suggested that precursors from non-neurogenic tissues require signals provided in culture to acquire the competence to differentiate into neurons.

To determine how rapidly cortical cells acquired the competence to differentiate into neurons in culture, cells were isolated and cultured in growth medium for various times, allowed to differentiate in differentiation medium and then evaluated for the presence of neurons. In control cultures, cells were cultured in 10% fibroblast bovine serum or 5 ng/ml recombinant platelet-derived growth factor (PDGF) instead of FGF-2. After three days in FGP-2, the occasional neuron was observed in cortical cultures and this number gradually increased with lengthening exposure to FGF-2. By 4 weeks both cultures had been passaged 3 times and roughly 10% of the cells formed neurons when induced to differentiate. Although cells were rapidly recruited into cell cycle in serum or PDGF, no neurons were formed (not shown). Cultures were also treated with BrdU for the first 10 days and the newly generated neurons were evaluated for evidence of cell division. All neurons scored were labeled (>99%). This demonstrated that exposure to FGF-2 was necessary for the recruitment of neuron-competent precursors and that proliferation invariably accompanied the recruitment process.

Neuron-competent progenitors are found in areas distant from the proliferative zones of the anterior SVZ. Cortical gray matter contains a small population of endogenously dividing glial progenitors, but the underlying subcortical white matter and ventricular zone have relatively abundant populations of dividing cells. Although it is suspected that many of the "cortical" progenitors were, in fact, derived from this underlying proliferative zone, it was also possible that contaminating cells from the more rostral neurogenic areas of the lateral ventricle may have been present in the cortical preparations. For example, others have shown that the adult optic nerve retains an active population of glial progenitors and the optic nerve rostral to the optic chiasma can be easily harvested without risk of contamination from the SVZ of the lateral ventricle.

To determine if there were progenitors in the optic nerve with a latent ability to generate neurons, optic nerve was harvested, dissociated and fractioned. Low-buoyancy cells were cultured for 14 days in the presence of high FGF-2 and then allowed to differentiate for an additional 14 days. BrdU was added during the last 72 hours of FGF-2 treatment (day 14). On day 28, cultures were calculated for the presence of neurons (β Tubulin) and those neurons present were scored for BrdU-immunoreactivity. Although many glia rapidly differentiated in the primary culture, clusters of proliferative precursor-like calls were readily detected. After several weeks in culture, a small but significant minority of these responding cells were able to generate β Tubulin-positive neurons when induced to differentiate (0.8% +/− 0.3% of the total population, mean +/− s.e.m., n=5). Neuronal markers such as β Tubulin, 200 kd neurofilament, and Tau were never detected in GFAP-positive or O4-positive glia, indicating that the neuron-like cells were authentic neurons rather than glia that inappropriately expressed neuronal markers. Neurons were often found in small clusters, suggesting a clonal derivation, and all cells, including neurons, were labeled with BrdU during the last 72 hours of FGF-2 treatment (<1 unlabeled cell per 50,000 total nuclei). This data indicates that all neurons were derived from proliferative precursors. The fact that these neurons are generated from cells isolated from the optic nerve dispels any concerns of contamination from known neurogenic zones and demonstrates that a latent neurogenic potential is retained by precursors from divergent regions of the adult brain.

Example 5

Regulation of ACSC Neurogenesis

The following experiments demonstrate the responsiveness (i.e., inducibility of differentiation), in vitro, of ACSC when exposed to retinoic acid and a variety of neurotrophins.

Cell Culture. For proliferating conditions, clonal stem cells (AP14) were cultured in Dulbecco's Modified Eagles Medium/Ham's F12 (DMEM/F12, 1:1) containing N2 supplement (Gibco BRL, Gaithersburg, Md.) and 20 ng/ml rhFGF-2 (provided by A. Baird, Prizm Pharmaceuticals Inc., La Jolla, Calif.). Culture dishes (Becton Dickinsin Labware, Lincoln Park, N.J.) were coated with polyomithine and mouse laminin as previously described by Ray, et al., Proliferation, differentiation and long-term culture of primary hippocampal neurons, *Proc Natl Acad Sci USA* 90:3602–3606 (1993). For differentiation experiments, cells were plated into polyornithine/laminin coated glass chamber slides (Nunc, Naperville, Ill.) at a density of 2.5—103 per cm2. The cells were incubated for 24 hrs in normal N2 medium containing 20 ng/ml FGF-2, and then the medium was replaced by N2 medium containing 0.5% fibroblast bovine serum (FBS) and 0.01% DMSO (control solvent) or 0.5 mM all-trans retinoic acid (Sigma, St. Louis, Mo.). For further differentiation, the medium was replaced by N2 medium containing 0.5% FBS and one of the following: sterile water (control solvent), mouse 2.55 NGF (50 ng/ml, Boehringer Mannheim, Indianapolis, Ind.), rhBDNF (20 ng/ml, Alomone Labs, Jerusalem, Israel), rhNT-3 (40 ng/ml, Genentech, South San Francisco, Calif.). The medium was replaced every two days. For inhibition of the tyrosine kinase activity of the Trk receptors, K-252a (100 nM, Calbiochem, San Diego, Calif.) was added to the medium.

Reverse Transcription-PCR Analysis. Total RNA from stem cells was isolated using RNeasy Total RNA Kits (Qiagen, Chatsworth, Calif.) according to manufacturer's instructions. Fifty nanograms of total RNA was reverse transcribed using avian myeloblastosis virus reverse transcriptase (Promega, Madison, Wis.) with random hexamers (10 mM) as primers in a 20-ml reaction mixture. For PCR amplification, two sets of specific oligonucleotide pairs (0.5 mM) were used: one directed to the transcript of interest, and one for a constitutively expressed transcript, either ribosomal protein L27 or L27a. Reactions were performed in a 100-ml reaction mixture containing 10 mM Tris-Cl (pH 8.4), 50 mm KCl, 1.5 mM MgC12, 200 mM each of the four dNTPs, 2 mCi of [a-32P]dCTP and 5 units of Taq polymerase (Promega) using a thermal cycler (Perkin-Elmer, Foster City, Calif.) with a regimen of 1 min at 94° C., 2 min at 60° C. (55° C. for trk receptors) and 2 min at 72° C. for 23 cycles Fifty microliters of each reaction was analyzed by electrophoresis on 8% polyacrylamide gels followed by autoradiography. Primers for the rat ribosomal protein L27 and L27a were used as an internal control to show that the amount of input RNA was the same for each sample. Under these conditions, the L27 amplification product was directly proportional to the amount of input RNA, up to 50 ng total RNA. Oligonucleotide primers used are as follows:

```
rat ribosomal protein L27:
5' primer: 5'-GAACATTGATGATGGCACCTC-3'    (SEQ ID NO:1),
3' primer: 5'-GGGGATATCCACAGAGTACC-3'     (SEQ ID NO:2),
189 bp amplified product;
```

-continued

```
rat ribosomal protein L27a:
5' primer: 5'-ATCGGTAAGCACCGCAAGCA-3'      (SEQ ID NO:3),
3' primer: 5'-GGGAGCAACTCCATTCTTGT-3'      (SEQ ID NO:4),
235 bp amplified product;

rat trkA:
5' primer: 5'-CACTGGGTGGCAGTTCTCTT-3'      (SEQ ID NO:5),
3' primer: 5'-CATGTACTCGAAGACCATGA-3'      (SEQ ID NO:6),
368 bp amplified product;

rat trkB:
5' primer: 5'-GTTGCTGACCAAACCAATCG-3'      (SEQ ID NO:7),
3' primer: 5'-CATGTACTCAAAGACCATGA-3'      (SEQ ID NO:8),
597 bp amplified product;

rat trkC:
5' primer: 5'-CTGAAGGATCCCACCTTGGC-3'      (SEQ ID NO:9),
3' primer: 5'-CATGTATTCAAAGACCATGA-3'      (SEQ ID NO:10),
141 bp amplified product;

rat p75NGFR:
5' primer: 5'-CCCTGCCTGGACAATGTTAC-3'      (SEQ ID NO:11),
3' primer: 5'-CTGGGCACTCTTCACAC-3'         (SEQ ID NO:12),
256 bp amplified product;

mouse NeuroD:
5' primer: 5'-GCATGCACGGGCTGAACGC-3'       (SEQ ID NO:13),
3' primer: 5'-GGGATGCACCGGGAAGGAAG-3'      (SEQ ID NO:14),
317 bp amplified product;

rat p21:
5' primer: 5'-GCCCAAGATCTACCTGAG-3'        (SEQ ID NO:15),
3' primer: 5'-GTGGGCACTTCAGGGCTTTC-3'      (SEQ ID NO:16),
290 bp amplified product;

rat c-fos:
5' primer: 5'-GGGTTTCAACGCGGACTAC-3'       (SEQ ID NO:17),
3' primer: 5'-GTTGGCACTAGAGACGGA-3'        (SEQ ID NO:18),
166 bp amplified product.
```

BrdU Labeling and Visualization. Cells plated as described above were treated with BrdU (10 mM, Sigma) for 24 hrs before fixation. Then the cells were fixed with tris-buffered 4% paraformaldehyde for 15 min. incubated with tris-buffered 0.6% $H_2O_2$ for 30 min, and treated with 50% formamide/2xSSC for 2 hrs followed by a 30-min incubation in 2N HCl, and a neutralization in 0.1M borate ($Na_2B_4O_7$) for 10 min. Cells were incubated with a-BrdU monoclonal antibody (1:400, Boehringer Mannheim) overnight at 4° C., and incubated with biotinylated horse anti-mouse secondary antibody (1:80, Jackson Immunoresearch, West Grove, Pa.) for 1 hr. Reactive cells were visualized with the avidin/biotin-peroxidase system (Vectastain Elite, Vector Laboratories, Burlingame, Calif.) and diaminobenzidine.

Immunofluorescence. An immunofluorescent staining was performed as previously described (Gage F H, Ray J, Fisher L J (1995a) Isolation, characterization, and use of stem cells from the CNS. Annu Rev Neurosci 18: 159–192. or Gage F H, Coates P W, Palmer T D, Kuhn H G, Fisher L J, Suhonen J O, Peterson D A, Suhr S T, Ray J (1995b) Survival and differentiation of adult neuronal progenitor cells transplanted to the adult brain. Proc Natl Acad Sci USA 92:11879–11883.) Briefly, after fixation with 4% paraformaldehyde in PBS, cells were incubated with primary antibodies overnight at 40 C. Then the cells were incubated for 1 hr with secondary antibodies (Jackson Immunoresearch) conjugated to fluorescein isothiocyanate, or cyanin-3. Primary antibody concentrations used are as follows (mo= mouse monoclonal, rb=rabbit polyclonal, gp=guinea pig polyclonal): mo a-MAP2abc, 1:5000 (Sigma), mo a-MAP2ab, 1:500 (Sigma), mo a-p75NGFR, 1:10 (192-IgG hybridoma supernatant, a gift from C. E. Chandler, Stanford Univ., Stanford, Calif.), rb a-c-Fos (4),1:4000 (Santa Cruz Biotechnology, Santa Cruz, Calif.), gp a-GFAP, 1:500 (Advanced Immunochemicals, Long Beach, Calif.), rb a-GABA, 1:5000 (Sigma), mo a-TH, 1:500 (Boehringer Mannheim), rb a-calbindin 1:1000 (SWant, Bellinzona, Switzerland). Labeled cells were visualized using confocal scanning laser microscopy (Zeiss Axiovert, Thornwood, N.Y. and Bio-Rad MRC1000, Hemel Hempstead, UK) and color images were generated using Adobe Photoshop (Adobe Systems, Mountain View, Calif.). Both the average percentage and the absolute number +/− SEM of immunofluorescent cells were determined by counting 10 or 50 high power fields (20x) visualized under fluorescence. The total number of cells was counted using nuclear counterstaining with 4',6diamidino-2-phenylindole (DAPI, Sigma). Statistical analyses were carried out using ANOVA test.

Histochemical Staining for AChE. Cholinergic cells were identified by histochemical staining for AChE by a modification of the staining method of Geneser-Jensen and Blackstadt. Distribution of acetylcholinesterase in the hippocampal region of the guinea pig. I. Entorhinal area parasubiculum, and pre-subiculum, Z Zellforsch 114:460–481(1971). Following fixation of the cultures in 4% paraformaldehyde, the cells were incubated for 7 days at 4° C. in the presence of the AChE substrate solution composed of the following: 4 mM acetylthiocholine iodine, 0.2 mM ethopropazine, 2 mM copper sulfate, 10 mM glycine, and 10 mg/ml gelatin in 50 mM acetate buffer (pH 5.0). For visualization of the reaction product, cells were washed with water, treated for 1 min with 1.25% $Na_2S$, and washed again with water. Cells were then treated for 1 rain with 1% $AgNO_3$ and washed with water.

Retinoic acid has been shown to be effective in promoting a variety of cell differentiation programs. To determine its effects on neuronal differentiation in populations derived from single stem cells, several clonal stem cell cultures (i.e., ACSC) were treated with increasing concentrations of RA. It has previously been shown that simple withdrawal of FGF-2 from the proliferative cultures triggered some neuronal differentiation, as evidenced by the expression of neuron-specific markers. The first neuronal markers to appear included microtubule-associated protein 2ab (Map2ab), microtubule-associated protein 5 (Map5), and type III b-tubulin. Withdrawal of FGF-2 and treatment with 500 nM RA plus 0.5% FBS for 6 days followed by an additional 6 days in 0.5% serum alone more than tripled the number of Map2ab-immunoreactive (IR) neurons relative to growth factor withdrawal and treatment with 0.5% serum alone. Surprisingly, the presence of RA was only necessary in the first six days following withdrawal of FGF-2 yet the effects of RA on neuronal differentiation were most apparent 12 or more days following FGF-2 withdrawal.

An early event in neuronal differentiation involves alterations in the expression of cell-cycle proteins and exit from the cell cycle. Cell cycle proteins such as cyclins and cyclin-dependent-kinases (CDKs) play a key role in regulating proliferation. Cyclin-CDK activity can be modulated by tumor suppressors, such as pRb and p53, or CDK inhibitors, which include p21, p 16 and p27. Upregulation of p21 is known to be involved in the NGF-stimulated differentiation of PC12 cells, and in many neuroblastoma cell lines, RA treatment alone is sufficient to induce growth arrest.

In ACSC cultures, low levels of p21 mRNA were detectable in proliferating cells; however, following RA treatment there was a significant yet gradual increase in p21 that peaked after roughly 5 days of RA treatment. Upregulation of p21 was accompanied by a decrease in the number of dividing cells as evidenced by BrdU incorporation. Cultures were treated with RA for 2, 4, or 6 days and then pulsed with 10 mM bromodeoxyuridine (BrdU) for 24 hrs on the last day of RA treatment. Cells were then fixed and processed for BrdU immunocytochemistry. In the presence of RA, there was a dramatic change in cell morphology, and a gradual decrease in the total number and proportion of BrdU-positive cells. Within 6 days of RA treatment, most of the phase-bright cells extended elaborate processes and only 29% of the cells were BrdU-positive, whereas in the serum-alone control treatment most of the cells continued to proliferate and retained rudimentary process morphology. In proliferative FGF-2-stimulated controls, more than 95% of the cells were labeled every 24 hrs.

Although proliferation decreased in response to RA, it is possible that the few remaining proliferating cells were contributing to the increase in neurons observed following RA treatment. To determine if RA induced a selective expansion of neuronal precursors, parallel cultures were treated with RA for 6 days followed by an additional 6 days in 0.5% serum alone. One set of cultures was fixed on days 2, 4, 6, 8, 10, and 12 and stained with 4,6-diamidino-2-phenylindole (DAPI) and the total number of nuclei was counted. Additional cultures were pulsed with BrdU for 72 hrs on days 0–3, 3–6, 6–9 or 9–12. The cultures were then fixed on day 12 and evaluated for the proportion of Map2ab-IR cells that had incorporated BrdU. Less than one third of the Map2ab-IR divided in the three days immediately following the start of RA treatment. Less than 5% of the Map2ab-IR cells divided during days 3–6 of treatment and fewer than 0.5% of the Map2ab-IR neurons divided after 6 days of RA treatment. To examine the earlier time points more carefully, the experiment was performed a second time but pulsed with BrdU for 24 hrs immediately upon application of RA or for 24 hours one day following the application of RA. In this case, 19 +/− 3% of the neurons were labeled in the first 24 hours and only 3 +/− 1% of the neurons were labeled in the second day following treatment. These findings indicate that a majority of the neurons generated by RA stimulation were induced to exit the cell cycle immediately upon RA treatment.

The activation of region and cell type-specific transcription factors often precedes or accompanies exit from cell cycle in developmental fate choice and differentiation events. NeuroD is one of the neuronal differentiation genes in vertebrates which encodes a basic-helix-loop-helix protein of the same family as atonal. It is transiently expressed in subsets of post-mitotic neurons in the CNS and peripheral nervous system (PNS) and causes premature differentiation of neurons when expressed ectopically. To determine if RA influenced NeuroD expression, mRNA was examined after RA treatment. In controls (cells proliferating in the presence of FGF-2), low levels of NeuroD mRNA were detectable. However, within 24 hrs of FGF-2 withdrawal and RA treatment, the expression of NeuroD increased and remained elevated for the 6 days of treatment. Withdrawal of FGF-2 and treatment with 0.5% FBS alone, on the other hand, resulted in decreased expression of NeuroD.

Retinoic acid also upregulates the expression of trkA, trkB, trkC and p75NGFR mRNA. Recent studies demonstrate that neurotrophins (NT) play an important role in neuronal development. It seems likely that differentiation in response to RA may involve one or more of the neurotrophin receptors. The expression of mRNA for trkA, trkB, trkC and p75NGFR was examined by RT-PCR analysis. Primers were designed to recognize only the mRNA for full-length Trk receptors, i.e., only those receptors capable of signal transduction via an intact C-terminal catalytic domain. Cells proliferating in the presence of FGF-2 expressed detectable amounts of trkC mRNA, and very low levels of trkA and trkB mRNA. However, no p75NGFR could be detected. Following RA treatment, mRNA for trkA, trkB, and trkC increased gradually and reached a plateau after 5 days, whereas, p75NGFR dramatically increased over the entire 7-day time course. The induction of neurotrophin receptors in the stem cell cultures suggested that treatment with an appropriate neurotrophin could have a significant effect on neuronal differentiation.

RA treatment also results in neurotrophin-dependent induction of c-fos. Transient and rapid induction of immediate early genes such as c-fos is a well-characterized response to extracellular stimuli in neural cells. c-fos is induced after neurotrophin treatment in cultured fibroblast hippocampal or cortical cells and the signaling cascade following c-fos induction is considered to be integral to subsequent steps in differentiation. To determine whether upregulation of mRNAs for trk receptors and p75NGFR observed in the stem cell cultures results in the acquisition of functional Trk-dependent stimulation of c-fos, mRNA was examined by RT-PCR analysis after stimulating RA-treated cells with neurotrophins. When proliferating controls were treated with NGF or BDNF, the induction of c-fos mRNA was minimal. NT-3, however, slightly increased the expression of c-fos, consistent with the low amounts of trkC mRNA detected in the proliferating cell cultures. Treatment with 0.5% FBS alone provided a subtle increase in neurotrophin responsiveness whereas pretreatment with RA for 6 days increased the baseline expression of c-fos mRNA as well as the induced level of c-fos following stimulation with NGF, BDNF, and NT-3. Pretreatment with K-252a, a selective inhibitor of Trk receptor tyrosine kinase, blocked c-fos induction by each neurotrophin, confirming that induction of c-fos was mediated by receptor tyrosine kinase signaling.

To determine which cells were responding to neurotrophins, stimulated cultures were double labeled for c-Fos and microtubule-associated protein (MAP)2abc, MAP2ab, p75NGFR or GFAP. The MAP2 protein has three isoforms that are developmentally regulated. In differentiating neurons in vivo and in vitro, MAP2c appears before MAP2a and 2b. The antibodies used here recognize either all three forms (MAP2abc) and would detect MAP2 in both immature and mature neurons or recognize only the a and b forms of MAP2 (MAP2ab) expressed by more mature neurons.

Very few c-Fos-positive cells were observed in proliferating cultures. Treatment with 0.5% FBS alone produced a small increase in the number of cells responding to each neurotrophin, and the number of c-Fos-positive cells was significantly enhanced when cells were treated with RA for 6 days prior to stimulation by neurotrophins. The RA-mediated increase in c-Fos-positive cells was particularly noticeable in BDNF and NT-3-treated cultures. Combined stimulation by two or three neurotrophins had no additive effect on the number of c-Fos-positive cells. When immature MAP2abc-positive cells were examined, only 3% (11/400) induced c-Fos in response to neurotrophins. On the other hand, 47% (186/400) of the more mature MAP2ab-positive neurons were c-Fos-positive following NT stimulation. None (0/400) of the c-Fos-positive cells were GFAP-positive astrocytes, suggesting that c-Fos responses were occurring predominantly in the more mature MAP2ab-positive neurons. Although p75NGFR-positive cells were abundant, very few (7/400) were also c-Fos-positive, suggesting that p75NGFR plays little, if any, role in signaling by these three neurotrophins in stem cell-derived progenitors.

Treatment with neurotrophins after RA priming promotes the maturation of newborn neurons. It has previously been shown that neurotrophins had limited affects on promoting differentiation in the absence of RA stimulation. However, in this example the dramatic upregulation of the Trks led to the speculation that NTs would be more effective following RA treatment. To determine how the RA-induced responsiveness to neurotrophins affected neuronal differentiation, ACSC cultures were first treated with RA for 6 days, then RA was withdrawn and either NGF, BDNF or NT-3 was added for an additional 6 or 12 days. Map2ab expression was used as an indication of the total number of neurons present and a limited set of transmitter phenotypes was evaluated as an indication of neuronal maturation. Immunofluorescent staining for gamma-aminobutyric acid (GABA), or tyrosine hydroxylase (TH) was used along with acetylcholinesterase (AChE) histochemical staining to identify the respective neuronal phenotypes. Cells were also evaluated for expression of calbindin, a calcium binding protein expressed by hippocampal granule cells in vivo.

In proliferating cultures, very few cells (<0.1%) were immunoreactive for MAP2ab or calbindin. No GABAergic, cholinergic, or dopaminergic cells were detected. When cultures were treated with RA for 6 days and then RA was withdrawn for an additional 6 days, the number of MAP2ab-positive cells increased 3-fold. Neurotrophin treatment had no effect on the total number of neurons. In contrast, neurotrophin treatment had a significant effect on the number of neurons expressing GABA, AChE, TH or calbindin. The most frequently encountered phenotype, GABA, was increased by BDNF and NT-3, but not NGF. Similarly, BDNF and NT-3, but not NGF, increased the number of TH-positive or calbindin-positive cells. BDNF was the most effective agent for increasing the number of AChE-positive cells, although NT-3 and NGF treatment provided small increases over control cultures.

Accordingly, the forgoing example demonstrates that ACSC can be induced to differentiate in vitro by treatment with retinoic acid and one or more neurotrophins.

Example 6

Intra-species Allogeneic Retinal Transplantation of ACSC

Prior attempts to transplant neural cells into the diseased retina have met with little success, in large part because donor cells do not integrate with those of the host. In order to test whether the use of neural progenitor cells would modify this outcome, clonally derived, adult rat hippocampal progenitor cells (AHPCs, (i.e., invention ACSC isolated from hippocampal tissue)), genetically modified to express green fluorescent protein (GFP), were injected into the eyes of dystrophic Royal College of Surgeons (RCS) rats (an extensively studied model of retinal degeneration). More specifically, hippocampal progenitor cells were clonally derived from adult Fischer 344 rats, genetically modified to express the modified jellyfish (Aequorea victoria) enhanced green fluorescent protein GFP (eGFP), as more thouroughly detailed below. In some cases, the cells were pulsed with BrdU (5/Am, 2 days) prior to transplantation.

AHPCs were cultured and differentiated as follows. Primary adult hippocampal progenitor cultures were prepared from hippocampal tissues of 3-month-old female Fisher 344 rats as described by Gage, F. H., Ray, J. & Fisher, L. J., Isolation, characterization, and use of stem cells from the CNS, *Annu. Rev. Neurosci.*, 18:159–192 (1995). Dissociated cells were cultured on polyornithine/laminin coated dishes using a mixture of DMEM/Ham+ F-12 (1:1) supplemented with N2 (Gibco) and 20 ng/ml FGF-2 (human recombinant, prepared in *E. coli*, kindly provided by A. Baird). Individual cells were genetically marked using replication-defective retroviral vectors expressing GFP from a tetracycline-regulatable, minimal human cytomegalovirus immediate early promoter fused to a tet-operator (NIT-GFP). Cloned cultures were derived from bulk-injected cultures. Each AHPC clone carried a neomycin phosphotrnsferase gene (neo) and the enhanced green fluorescence protein (GFP) gene. To confirm the lineage potential of each clone prior to grafting, AHPCs were induced to differentiate in 4-well chamber slides at a cell density of 2,500 cells per $cm^2$ by withdrawal of FGF-2 and treatment for 14 days in DMEM/F12+N2, supplemented with 0.5 $\mu$M all-trans retinoic acid and 0.5% fibroblast bovine serum. These conditions favor the differentiation of neurons, astrocytes, and oligodendrocytes in a single well.

AHPCs were prepared for grafting in the following manner. Cultured AHPCs were harvested with trypsin, washed with high glucose Dulbecco's PBS (D-PBS, Gibco), and suspended at a density of 100,000 cells per $\mu$l in D-PBS containing 20 ng of FGF-2 per ml.

Recipient animals and transplantation. Pigmented dystrophic RCS rats, age 3–28 days, received injections of AHPCs into the vitreous or subretinal space under general (Ketamine/xylazinc) and topical (proparacaine) anesthesia and under direct observation using coaxial illumination via a binocular surgical microscope (Miller) through a dilated pupil (topical tropicamide 1%). The injections were made via a beveled glass micropipette (outer diameter of 1 mm) connected to a 50-μl Hamilton microsyringe via polyethylene tubing. A total of 50,000 cells in 1 μl of DMEM/F12 media were injected. As a control, cells that were freeze-thawed 3 times (from −70° C.) were also injected.

Tissue preparation and histology. Recipient animals were sacrificed with an overdose of sodium pentobarbitol at 1, 2, 4, and 8 weeks post-transplantation. The eyes were removed and immersion-fixed with 4% paraformaldehyde for 4 hours at 4° C. The anterior segment and lens were then removed, and the posterior segment cryoprotected in 30% sucrose/PBS overnight at 4° C., followed by embedding in OCT and subsequent sectioning at 7–14 μm on a cryostat. Sections were processed for haematoxilin and eosin, anti-BrdU (1:200), anti-synaptophysin (1:200) and anti-GFP (1:200), followed by reaction with Cy3-conjugated secondary antibodies, thus allowing co-localization of the markers with the endogenous GFP expressed in transplanted AHPCS.

Morphology. Tissue sections were viewed under fluorescence microscopy to identify donor cells, and were compared with adjacent sections stained with H&E to highlight the overall retinal cytoarchitecture, including the retinal laminae. Confocal microscopy was carried out on a subset of material that was of particular interest.

Clonally derived AHPCs from adult Fischer 344 rats, which were genetically modified to express green fluorescent protein (GFP), and also labeled with BrdU in some cases, were-transplanted into both immature (3 days postnatal, P3) and mature (21–28 days postnatal, P21–28) dystrophic eyes of RCS rats. Following transplantation, donor-derived cells were found to maintain high levels of GFP expression. One week post-grafting, AHPCs could be seen adhering to the vitreal surface of the graft recipient (i.e., host) eye, migrating into the host retina, and taking up residence within specific retinal laminae of the host. In some cases, grafted cells were seen in the host photoreceptor layer, and when examined with anti-BrdU, were found to be double labeled with GFP and BrdU, confirming the cells' derivation from the transplanted AHPCS. The GFP+cells were quite striking in appearance and were easily distinguished from host autofluorescence in the recipient. No evidence of viable donor cells, or host GFP expression, was seen following injection of freeze-thawed GFP+AHPCs (negative control).

At subsequent times post-grafting, widespread migration of grafted AHPCs into the host retina was seen. At 4 weeks post-grafting, numerous cells were seen to exhibit neuronal-like morphologies throughout the various laminae of the host retina. These cells took up residence in all nuclear layers of the host retina, in most cases respecting the cellfree plexiform layers, where they often had elaborated arbors. Moreover, when grafted cells were found to extend numerous neuronal-like processes, these processes often resembled those of normal retinal neurons. These processes were found to project preferentially either laterally (i.e., resembling horizontal cells), or radially (i.e., resembling bipolar cells). These morphologies may be due to intrinsic or extrinsic developmental factors, or may result from the restrictions imposed by the local retinal cytoarchitecture. Widespread migration and morphological integration of AHPCs were also seen at 8 weeks post-grafting. The degree of retinal integration, however, was not entirely uniform: in some regions the host retinal cytoarchitecture was preserved, while elsewhere the laminar organization was noticeably distorted in association with high numbers of grafted cells. Similar to results observed at 4 weeks post-grafting, AHPCs developed extensive neurite-like projections, which extended throughout the host retina, including the plexiform layers. The apparent increased density of GFP+ processes at successive time points indicate that AHPCs continue to develop along a neuronal-like pathway for at least 8 weeks post-grafting. Significantly, no evidence of immunological rejection (i.e., infiltration of leukocytes) was observed over the course of this study.

When subsequently examined, the retinas of these animals exhibited widespread migration of green fluorescent protein-expressing (GFP+) donor cells into all layers of the host retina. The transplanted cells survived for at least 2 months post-grafting, without provoking a prominent immune response. Furthermore, GFP+cells aligned themselves with the existing cytoarchitecture and exhibited extensive arborization in configurations appropriate for retinal neurons. Similar results were obtained with both immature and visually mature, recipient animals. These results indicate that the dystrophic retina can be substantially repopulated by using a line of adult-derived, neural progenitor or stem cells from an allogeneic donor, and that these cells can be functionally integrated, since they arborize extensively within the host neuropil. Thus, the ability of transplanted AHPC cells to migrate into, and differentiate within, the mature retina during the active phase of neuronal degeneration is demonstrated.

This study shows that cells derived from adult hippocampus are capable of migrating in large numbers into all layers of the dystrophic neuroretina, including, in some cases, into the photoreceptor layer. Following migration, transplanted AHPCs exhibit a surprising ability to differentiate into neurons with morphological characteristics suggestive of native retinal cell types. The cell processes extended by AHPCs within the retina tend to resemble the neuritic profiles of specific retinal neurons, including sublamina-specific ramifications within the inner plexiform layer suggestive of bipolar and horizontal cells. Furthermore, the presence of distinct bands of diffuse GFP-derived fluorescence along these sublaminar zones is suggestive of a network of fine terminals within the host neuropil. These data indicate that AHPCs are capable of functional integration into the retina.

One of ordinary skill in the art of neuronal transplantation will appreciate how to practice the present invention and to manipulate AHPCs to account for such factors as functional capability, host immunological tolerance, and the long-term consequences of grafting (e.g., promoting graft survival and controlling undesired proliferation). The demonstration here of survival in a dystrophic, allogeneic environment for at least 2 months, indicates the ultimate immunological success of progenitor cell transplantation to the diseased central nervous system.

Example 7

Xenogeneic Retinal Transplants

The survival of adult rat-derived, hippocampal neural progenitor cells transplanted into the dystrophic mouse retina was investigated. These transplanted cells were capable of integrating into the murine host retina and of maintaining expression of the green fluorescence protein (GFP) gene inserted into the progenitor cells.

Methodol gy. Neural progenitor cells, cultured from the hippocampus of adult Fischer 344 rats, were genetically modified to express GFP and a clonal cell line was isolated, as previously described. These cells were then transplanted into the vitreous of 7-day-old "rd-1" mice (50,000 cells in 1 μl), without immunosuppression. After 2–4 weeks post-transplant, the eyes were removed and sectioned.

Results and Discussion. At both survival times (2 weeks and 4 weeks post-transplant), large numbers of GFP+ cells were found in the vitreous of host mice. Many cells were adherent to the inner surface of the retina, where they extended long, axon-like processes. In some cases, cells were found to have migrated into the host retina, where they developed neuron-like phenotypes, and extended numerous processes into the host neuropil.

Rat, adult neural progenitor cells transplanted to a xenogeneic environment without immunosuppression are capable of surviving for at least 4 weeks and maintaining expression of a GFP marker. These cells can also migrate into the host retina, where they developed neuron-like phenotypes. The use of xenogeneic, pluripotent progenitor cells as a source of donor tissue in transplantation protocols offers a viable new technology for studying and manipulating neural development and neural tissue plasticity, and repairing damaged central nervous system (CNS) tissue. In the case of human disease, the present technology will enable the use of xenogenic, neural tissue, such as pig-derived neural progenitor cells, to treat retinal and other neurological diseases and injuries involving neuronal loss.

Example 8

Widespread Integration and Survival of Adult-derived Neural Progenitor Cells in the Developing Optic Retina AHPC culture and differentiation. Primary adult hippocampal progenitor cultures were prepared from hippocampal tissues of 4-to 6-month-old female Fisher rats as previously described in Example 5. Dissociated cells were cultured on polyornithine/laminin coated dishes using a mixture of DMEM/Ham's F12 (1:1) supplemented with N2 (Gibco) and 20 ng/ml FGF-2. Individual cells were genetically marked using replication-defective retroviral vectors and two previously extensively characterized multipotent normal diploid clones, PZ5 and Zn3, were used in the present studies. Each AHPC clone carried a neomycin phosphotransferase gene (neo) and either a cytoplasmic β-Gal gene or a nuclear localized β-Gal gene. To confirm the lineage potential of each clone prior to grafting, AHPCs were induced to differentiate in 4-well chamber slides at a cell density of 2,500 cells per cm² by withdrawal of FGF-2 and treatment for 14 days in DMEM/F12+N2, supplemented with 0.5 M all-trans retinoic acid and 0.5% fibroblast bovine serum. These conditions have been demonstrated to favor the differentiation of neurons, astrocytes and oligodendrocytes in a single well.

Preparation of cells for grafting. Cultured AHPC or, β-Gal marked normal diploid skin fibroblasts were harvested with trypsin, washed with high glucose Dulbecco's PBS (D-PBS, Gibco), and suspended at a density of 100,000 cells per ml in D-PBS containing 20 ng of FGF-2 per ml. A 10-ml Hamilton syringe with a 30-gauge beveled needle was used to slowly inject 3.0 ml of cells into the vitreous cavity of anesthetized adult rats (2 months old) and 1.5 ml into sub retinal space or vitreous cavity of neonatal rats (P0–P2). As a control, AHPC suspended in D-PBS at 100,000 cells per ml were freeze-thawed three times at −70° C. prior to injection.

Immunostaining. Cell phenotype was determined in vitro by double or triple immununo-staining in PBS containing 0.3% Triton X-100 and 3% horse or donkey serum (PBS/TS). Antibodies and concentrations were as follows: rabbit anti-β-Gal (1:5000, Cortex); mouse anti-microtubule-associated protein 2ab (MAP2ab, 1:500, Sigma); guinea pig anti-glial fibrillary acidic protein (GFAP, 1:500, Advanced Immunochemical); or mouse anti-galactocerebroside (GalC) diluted 1:10 (kindly provided by O. Boegler). For immunofluorescence, the primary antibody was detected with flourescein isothiocyanate or Texas red-labeled Donkey secondary antibodies (1:250, Jackson Immunochemicals, West Grove, Pa.). Eyes were harvested 2, 4, and 8 weeks after grafting and fixed in 4% paraformaldehyde. Twenty micron sections were cut using a cryostat and subsequently stained in PBS/TS with mouse anti-β-Gal antibody (1:5000 Promega) and/or guinea pig anti-GFAP (1:5000). For histochemical staining, the primary antibody was detected by the ABC method using a biotinylated horse anti-mouse antibody (Jackson Immunochemicals, West Grove, Pa.) diluted 1:80, and the immunohistochemical product was visualized using 3',3'-diaminobenzidine (DAB) as a chromagen and intensified using nickel. Detection of primary antibodies for fluorescent staining was performed as described herein. For nuclear counterstains, DAB-stained sections were treated with nuclear fast red.

Generation and grafting of engineered neural progenitor cells. AHPC populations were isolated from fresh hippocampal tissue, and single stem cells were isolated by clonal density plating under selection for a retrovirally transferred neo gene. The clonality of each culture was confirmed by the presence of a unique proviral band by Southern blot analysis, and karyotype analysis showed that the low-passage clonal populations consisted of normal diploid cells. Two clones were chosen at random from a number of clones previously characterized in detail (See, Palmer, T. D., Takahashi, 1., Gage, F. H., The rat hippocampus contains primordial neural stem cells. *Mol. Cell. Neurosci.* 8:389 (1997)). These clones, PZ5 and Zn3, carried retroviral marker genes encoding either cytoplasmic or nuclear localized , β-galactosidase (β-Gal), as described in Adam, M. A., et al., Internal initiation of translation in retroviral vectors carrying picornavirus 5' nontranslated regions, *J. Virol.* 65: 4985–4990 (1991), and Bonham, L., et al., Prolonged expression of therapeutic levels of human granulocyte colony-stimulating factor in rats-following gene transfer to skeletal muscle, *Hum. Gene Ther.* 7:1423–1429 (1996), respectively. The cell populations were also extensively evaluated for the presence of replication competent helper virus using both XC and marker-rescue assays and were free of detectable helper virus (<1 per 10 ml). (See, Miller, A. D. & Buttimore, C., Redesign of retrovirus packaging cell lines to avoid recombination leading to helper virus production, *Mol. Cell Biol.* 6:2895–2902 (1986)).

When proliferating in the presence of FGF-2, the AHPCs were observed to have round, bright cell bodies with short, thin processes. Following differentiation in the presence of 0.5% serum and 500 nM all-trans retinoic acid, the cells extended long processes and many cells became immunoreactive for the neuronal marker microtubule-associated protein 2ab (Map2ab), the astrocyte marker glial fibrilary acidic protein (GFAP), or the oligodendrocyte marker galactocerebroside (GalC). These results confirm that the clones used in this work were able to generate all three lineages that exist in the central nervous system.

Three hundred thousand AHPCs were injected into the vitreous space of the adult rat eye, or 150,000 were injected into the sub retinal space or vitreous space of the newborn rat eye. Rats were sacrificed and eyes were processed for histology 2, 4 or 8 weeks later. Controls to validate LacZ as an AHPC-specific marker in vivo included injection of an equivalent number of LacZ-labeled fibroblasts, injection of purified β-galactosidase enzyme, or injection of freeze-thawed LacZ-labeled AHPCs (clone PZ5).

Evaluation of survival and phenotype of AHPCs following grafting. Four weeks following grafting into the vitreous cavity of adults, the AHPCs were found attached to the inner surface of the retina and formed a thin contiguous cellular layer in intimate contact with the nerve fiber layer. There was no notable disturbance of retinal morphology, and the cell lamina continued to express β-Gal beyond the last 8 week time point. Similarly, two weeks after grafting into pups' vitreous cavity, the cells also attached nondestructively along the inner surface of the retina, but in contrast to grafts in the adult eye, by 4 weeks, many surviving cells had migrated into and were well integrated within most layers of the retina. Although some areas along the injection tract showed the deposition of a cell bolus, most cells were evenly distributed as single cells or small groups of cells within each retinal layer. Similar distributions of cells were observed at 8 weeks indicating that cell survival and transgene expression remained relatively constant for at least 8 weeks, the latest time point evaluated. Contrary to the results observed for vitreous grafts, cells placed into the sub retinal space of 2-day-old rat pups disrupted the normal retinal architecture to an extent that, even in those areas not disrupted by the injection, few cells were observed to integrate into the retina The integration patterns and morphologies of the two AHPC clonal populations, PZ5 and Zn3, were similar. Strikingly, many of the grafted cells took on morphologies of neuroglial, amacrine, bipolar, horizontal, or photoreceptor cells and were located in retinal layers appropriate for each morphological phenotype. Many cells migrated as far as the outer nuclear layer, where some cells took on the distinct morphology of photoreceptor cells. No clear evidence of AHPC-derived ganglion-like cells was observed. To determine if the grafted cells expressed markers specific for authentic retinal cells, tissue slices were co-lableled for β-Gal and a variety of retina-specific markers including tyrosine hydroxylase, Thy-1.1, protein kinase C (PKC), Ret P1, and S100 protein. None of the grafted cells expressed markers specific for retinal cells with the exception of the occasional S100+, and PKC+ cell. However, this finding did not necessarily suggest authentic retinal cell fates since these markers are present in the occasional cell prior to grafting.

Control grafts provide a considerable level of confidence that the cells observed in vivo are graft derived. Control grafts of β-Gal-marked normal diploid skin fibroblasts did not integrate into the retina, but rather attached to the retinal surface. Although these cells formed an intimate and contiguous lamina with the retinal surface, no β-Gal immunoreactivity was transferred to retinal cells. Similarly, injection of 1,000–5,000 times more purified *E. coli* β-Gal enzyme (Sigma) than was produced by 300,000 marked AHPC (as determined by enzyme assay, as described in Sambrook, J., Fritsch, E. F., & Maniatis, T. in Molecular Cloning, Second Edition, section 16.6 (Cold Spring Harbor, N.Y., 1989)) into the pups' vitreous cavity or into adult cerebral cortex showed no β-Gal uptake by host neurons or glia 3 hours, 1 day or 3 days after injection. Similarly, injection of 300,000 freeze-thawed AHPC into the vitreous space demonstrated that enzyme leaking from damaged or dead cells was not taken up by host retinal cells. Since the cells were free of replication competent helper virus and donation of beta-galactosidase to host cells appeared to be highly improbable, it was concluded that all marked cells were graft-derived.

Thus, AHPC-derived progenitors responded to local retinal cues and adopted morphologically appropriate phenotypes for their final location. These results indicate that progeny from immature adult-derived stem cells can respond to local cues in several regions of the central nervous system.

Migration and acquisition of appropriate morphologies for each retinal layer suggest that local signals have a strong influence on both migration and phenotype. For example, following grafting of committed amacrine or ganglion cell lines or a putative Müller cell line into the eye of an E13 chick, other researchers have observed that these fate-restricted cells migrated to the proper position for their phenotypes. In the present example, hippocampus-derived cells presumably have no predisposition to acquire phenotypes appropriate for each retinal layer, yet they consistently migrated into the retina and acquired a "correct" and distinct morphology for each location. This migration may provide some evidence for alternative cues that are induced following grafting.

Thus it is demonstrated that stem cells derived from the adult hippocampus respond to a much wider range of migrational (i.e., spatial) and differentiative (i.e., temporal) environments than expected for their site of origin. In previous studies it has been shown that some cells in adult-derived hippocampal cultures could travel along the rostral migratory stream to the olfactory bulb where they differentiated into olfactory bulb neurons. This suggests that some of the cells were sufficiently immature to adopt non-hippocampal cell fates. Suhonen, J. O., Peterson, D. A., Ray, J. & Gage, F. H., Differentiation of adult hippocampus-derived progenitors into olfactory neurons in vivo, *Nature* 383:624–627 (1996).

The foregoing demonstrates that AHPC-derived progenitors responded to local retinal cues and adopted morphologically appropriate phenotypes for their final location. The data further indicate that progeny from immature adult-derived stem cells can respond to local cues in several regions of the central nervous system.

While the invention has been described in detail with reference to certain preferred embodiments thereof, it will be understood that modifications and variations are within the spirit and scope of that which is described and claimed.

That which is claimed is:

1. A method for isolating adult mammalian CNS-derived progenitor cells (ACPC) or adult mammalian CNS-derived stem cells (ACSC) directly from adult mammalian central nervous system (CNS) tissue, said method comprising (i) subjecting dissociated mammalian CNS tissue to at least one density gradient centrifugation, and (ii) collecting cells that have a density in the range of about 1.065 up to about 1.075 g/ml.

2. A method according to claim 1, wherein said method results in enrichment of ACPC.

3. A method according to claim 2, wherein said CNS tissue is whole brain, hippocampus, spinal cord, cortex, striatum, cerebellum, thalamus, hypothalamus, amigdyla, basal forebrain, ventral mesencephalon, optic nerve or locus ceruleus.

4. A method according to claim 2, wherein said ACPC differentiate In vitro in mitogen-free media into neurons but not glia.

5. A method according to claim 2, wherein said ACPC acquire pluripotency upon in vitro exposure to mitogen.

6. A method according to claim 5, wherein said pluripotency comprises the ability to differentiate into neurons and glia.

7. A method according to claim 1, wherein said method results in enrichment of ACSC.

8. A method according to claim 7, wherein said CNS tissue is hippocampus or ventricular-adjacent brain.

9. A method according to claim 7, wherein said ACSC can differentiate in vivo in mitogen free media into neurons, and glia.

10. A method according to claim 1, wherein said density gradient comprises PERCOLL™, FICOLL™ or sucrose.

11. A method according to claim 10, wherein said density gradient comprises PERCOLL™.

12. A method according to claim 11, wherein said density gradient comprises 50% PERCOLL™.

13. A method according to claim 1, wherein said cells have a density in the range of about 1.072 up to about 1.075 g/ml.

* * * * *

SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
gaacattgat gatggcacct c                                               21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
ggggatatcc acagagtacc                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
atcggtaagc accgcaagca                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
gggagcaact ccattcttgt                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
cactgggtgg cagttctctt                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
catgtactcg aagaccatga                                                 20

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence: Primer

<400> SEQUENCE: 7
gttgctgacc aaaccaatcg                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
catgtactca aagaccatga                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
ctgaaggatc ccaccttggc                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
catgtattca aagaccatga                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
ccctgcctgg acaatgttac                                                20

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 12
ctgggcactc ttcacac                                                   17

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 13
```

-continued

```
gcatgcacgg gctgaacgc                                              19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
gggatgcacc gggaaggaag                                             20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
gcccaagatc tacctgag                                               18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
gtgggcactt cagggctttc                                             20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 17
gggtttcaac gcggactac                                              19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
gttggcacta gagacgga                                               18
```